United States Patent
McConnell et al.

(10) Patent No.: US 12,409,301 B2
(45) Date of Patent: Sep. 9, 2025

(54) WEDGE-LOCK SHEATH RETENTION MECHANISM

(71) Applicant: BOSTON SCIENTIFIC SCIMED, INC., Maple Grove, MN (US)

(72) Inventors: Kevin McConnell, Minneapolis, MN (US); John McSweeney, Cork (IE); Eric Douglas Nygaard, Eden Prairie, MN (US); Daniel Patrick Sexton, Cork (IE); Nicholas Lee Tassoni, Ramsey, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 778 days.

(21) Appl. No.: 17/031,070

(22) Filed: Sep. 24, 2020

(65) Prior Publication Data
US 2021/0085924 A1     Mar. 25, 2021

Related U.S. Application Data

(60) Provisional application No. 62/904,864, filed on Sep. 24, 2019.

(51) Int. Cl.
*A61M 25/01*     (2006.01)
*A61M 25/00*     (2006.01)
*A61M 25/09*     (2006.01)

(52) U.S. Cl.
CPC ........ *A61M 25/0102* (2013.01); *A61M 25/09* (2013.01); *A61M 2025/0062* (2013.01); *A61M 2025/09125* (2013.01)

(58) Field of Classification Search
CPC ........ A61F 2/0095; A61F 2/9522; A61F 2/95; A61F 2/966–9662; A61B 2017/1205;
(Continued)

(56) References Cited

U.S. PATENT DOCUMENTS

| 4,932,959 | A | | 6/1990 | Horzewski et al. |
| 4,978,341 | A | * | 12/1990 | Niederhauser .......... F16L 37/05 604/256 |

(Continued)

FOREIGN PATENT DOCUMENTS

| CN | 105722546 A | 6/2016 |
| EP | 2213244 A1 | 8/2010 |

(Continued)

OTHER PUBLICATIONS

International Search Report and Written Opinion dated Jan. 13, 2021 for International Application No. PCT/US2020/052465.

*Primary Examiner* — Kathleen S Holwerda
*Assistant Examiner* — Serenity A Miller
(74) *Attorney, Agent, or Firm* — Seager, Tufte & Wickhem LLP

(57) ABSTRACT

A medical device system may include a sheath, a pusher wire, and a locking element. The pusher wire may be slidably disposed within a lumen of the sheath. The locking element may have a proximal end, a distal end, an intermediate region disposed between the proximal end and the distal end, and a lumen extending from the proximal end to the distal end. The locking element may have a first inner diameter adjacent to the distal end and a second inner diameter adjacent to the proximal end, the second inner diameter smaller than the first outer diameter. The distal end region of the locking element may be configured to freely slide over the sheath and when a proximal end region of the locking element is disposed over the sheath, the locking element may be configured to depress the sheath radially inwards.

18 Claims, 30 Drawing Sheets

(58) Field of Classification Search
CPC .......................... A61B 17/12109–12118; A61B 17/1214–12154; A61B 2017/22047; A61B 2017/22049; A61B 17/12022; A61M 2025/09125; A61M 2025/09116; A61M 25/0102; A61M 25/09

See application file for complete search history.

(56) References Cited

U.S. PATENT DOCUMENTS

| | | | | |
|---|---|---|---|---|
| 5,191,888 | A * | 3/1993 | Palmer | A61M 25/0905 604/533 |
| 5,851,189 | A * | 12/1998 | Forber | A61M 25/09041 604/528 |
| 6,096,022 | A * | 8/2000 | Laymon | A61M 25/0097 604/533 |
| 6,110,146 | A * | 8/2000 | Berthiaume | A61M 25/09041 604/103.05 |
| 6,231,543 | B1 | 5/2001 | Hegde et al. | |
| 7,618,398 | B2 * | 11/2009 | Holman | A61F 2/958 604/160 |
| 8,007,509 | B2 * | 8/2011 | Buiser | A61B 17/12145 606/198 |
| 8,568,416 | B2 | 10/2013 | Schmitz et al. | |
| 8,850,676 | B2 * | 10/2014 | Schmitt | A61M 25/09041 29/44 |
| 9,320,618 | B2 | 4/2016 | Schmitz et al. | |
| 2002/0121472 | A1 | 9/2002 | Garner et al. | |
| 2002/0128678 | A1 | 9/2002 | Peterson | |
| 2005/0119675 | A1 | 6/2005 | Adams et al. | |
| 2007/0293719 | A1 * | 12/2007 | Scopton | A61B 1/00098 600/106 |
| 2008/0275458 | A1 | 11/2008 | Bleich et al. | |
| 2011/0046657 | A1 * | 2/2011 | Guo | A61B 17/12113 606/200 |
| 2012/0071856 | A1 | 3/2012 | Goldfarb et al. | |
| 2014/0343592 | A1 | 11/2014 | Rosenschein et al. | |
| 2015/0250470 | A1 | 9/2015 | Vargas | |

FOREIGN PATENT DOCUMENTS

| | | |
|---|---|---|
| EP | 2467068 A1 | 6/2012 |
| JP | 2005506105 A | 3/2005 |
| JP | 2006180938 A | 7/2006 |
| JP | 2013540501 A | 11/2013 |
| WO | 2015134758 A1 | 9/2015 |

* cited by examiner

WEDGE-LOCK SHEATH RETENTION MECHANISM

CROSS-REFERENCE TO RELATED APPLICATIONS

This application claims the benefit of priority of U.S. Provisional Application No. 62/904,864 filed Sep. 24, 2019, the entire disclosure of which is hereby incorporated by reference.

TECHNICAL FIELD

The present disclosure pertains to medical devices and methods for manufacturing and/or using medical devices. More particularly, the present disclosure pertains to configurations of a system for securing a medical device within a sheath.

BACKGROUND

A wide variety of intracorporeal medical devices have been developed for medical use, for example, surgical and/or intravascular use. Some of these devices include guidewires, catheters, medical device delivery systems (e.g., for stents, grafts, replacement valves, etc.), and the like. These devices are manufactured by any one of a variety of different manufacturing methods and may be used according to any one of a variety of methods. There is an ongoing need to provide alternative medical devices as well as alternative methods for manufacturing and/or using medical devices.

SUMMARY

In a first example, a medical device system may comprise a sheath having a proximal end, a distal end, an intermediate region disposed between the proximal end and the distal end, and a lumen extending from the proximal end to the distal end, a pusher wire slidably disposed within the lumen of the sheath, and a locking element having a proximal end, a distal end, an intermediate region disposed between the proximal end and the distal end, and a lumen extending from the proximal end to the distal end. The locking element may have a first inner diameter adjacent to the distal end and a second inner diameter adjacent to the proximal end, the second inner diameter smaller than the first inner diameter. A distal end region of the locking element may be configured to freely slide over the sheath. When a proximal end region of the locking element is disposed over the sheath, the locking element may be configured to depress the sheath radially inwards.

Alternatively or additionally to any of the examples above, in another example, the lumen of the locking element within the proximal end region may reduce in diameter in a sloped manner towards the proximal end of the locking element.

Alternatively or additionally to any of the examples above, in another example, the lumen of the locking element within the distal end region may have a generally uniform inner diameter.

Alternatively or additionally to any of the examples above, in another example, the sheath may include a first slot and a second slot, the first and second slots extending distally from the proximal end of the sheath and extending less than an entire length of the sheath.

Alternatively or additionally to any of the examples above, in another example, the sheath may include a longitudinally extending slot extending distally from the proximal end of the sheath.

Alternatively or additionally to any of the examples above, in another example, the longitudinally extending slot may terminate at a circumferentially extending slit.

Alternatively or additionally to any of the examples above, in another example, the sheath may include an angled protrusion extending radially outward from an outer surface thereof.

Alternatively or additionally to any of the examples above, in another example, the angled protrusion of the sheath may reduce in diameter in a proximal direction.

Alternatively or additionally to any of the examples above, in another example, the locking element may include an angled protrusion extending radially inward from an inner surface of the lumen of the locking element.

Alternatively or additionally to any of the examples above, in another example, the angled protrusion of the locking element may reduce in diameter in a distal direction.

Alternatively or additionally to any of the examples above, in another example, the angled protrusion of the sheath and the angled protrusion of the locking element may be configured to cooperate to limit axial movement of the locking element.

Alternatively or additionally to any of the examples above, in another example, the locking element may further comprise a slot extending from a proximal end of the locking element to a distal end of the locking element, the slot extending through a thickness of a wall of the locking element.

Alternatively or additionally to any of the examples above, in another example, the slot may have a width that is greater than a width of the pusher wire and less than a width of the sheath.

Alternatively or additionally to any of the examples above, in another example, the locking element may comprise a plurality of circumferentially extending ribs extending from an outer surface thereof.

Alternatively or additionally to any of the examples above, in another example, the locking element may be formed from a more rigid material than the sheath.

In another example, a medical device system may comprise a sheath having a proximal end, a distal end, an intermediate region disposed between the proximal end and the distal end, and a lumen extending from the proximal end to the distal end, the sheath having a first slot and a second slot, the first and second slots extending distally from the proximal end of the sheath, extending less than an entire length of the sheath, and defining a first flexible arm and a second flexible arm, a pusher wire slidably disposed within the lumen of the sheath, and a locking element having a proximal end, a distal end, an intermediate region disposed between the proximal end and the distal end, and a lumen extending from the proximal end to the distal end, the locking element having a first inner diameter adjacent to the distal end and a second inner diameter adjacent to the proximal end, the second inner diameter smaller than the first inner diameter. A distal end region of the locking element may be configured to freely slide over the sheath. When a proximal end region of the locking element is disposed over a proximal end region of the sheath, the locking element may be configured to depress the first and second flexible arms radially inwards.

Alternatively or additionally to any of the examples above, in another example, the lumen of the locking element within proximal end region may reduce in diameter in a sloped manner towards the proximal end of the locking element.

Alternatively or additionally to any of the examples above, in another example, the lumen of the locking element within the distal end region may have a generally uniform inner diameter.

Alternatively or additionally to any of the examples above, in another example, the locking element may further comprise a slot extending from a proximal end of the locking element to a distal end of the locking element, the slot extending through a thickness of a wall of the locking element.

Alternatively or additionally to any of the examples above, in another example, the slot may have a width that is greater than a width of the pusher wire and less than a width of the sheath.

Alternatively or additionally to any of the examples above, in another example, the locking element may comprise a plurality of circumferentially extending ribs extending from an outer surface thereof.

Alternatively or additionally to any of the examples above, in another example, the locking element may have a generally uniform wall thickness from the proximal end to the distal end of the locking element.

Alternatively or additionally to any of the examples above, in another example, the locking element may have a first wall thickness adjacent the proximal end and a second wall thickness adjacent to the distal end, the first wall thickness greater than the second wall thickness.

In another example, a medical device system may comprise a sheath having a proximal end, a distal end, an intermediate region disposed between the proximal end and the distal end, and a lumen extending from the proximal end to the distal end, the sheath further comprising a longitudinally extending slot extending distally from the proximal end of the sheath, a pusher wire slidably disposed within the lumen of the sheath, and a locking element having a proximal end, a distal end, an intermediate region disposed between the proximal end and the distal end, and a lumen extending from the proximal end to the distal end, the lumen of the locking element having a generally hourglass shape. A distal end region of the locking element may be configured to freely slide over the sheath. When an intermediate region of the locking element is disposed over the sheath, the locking element may be configured to depress the sheath radially inwards.

Alternatively or additionally to any of the examples above, in another example, the longitudinally extending slot of the sheath may terminate at a circumferentially extending slit.

Alternatively or additionally to any of the examples above, in another example, the sheath may further comprise a first flap and a second flap adjacent the longitudinally extending slot.

Alternatively or additionally to any of the examples above, in another example, the locking element may have a first inner diameter adjacent the distal end and a second inner diameter adjacent to the intermediate region, the second inner diameter smaller than the first inner diameter.

Alternatively or additionally to any of the examples above, in another example, the second inner diameter may be generally constant and extends between a flared distal end region and a flared proximal end region.

In another example, a medical device system may comprise a sheath having a proximal end, a distal end, an intermediate region disposed between the proximal end and the distal end, and a lumen extending from the proximal end to the distal end, the sheath further comprising an angled protrusion extending radially outward from an outer surface thereof, a pusher wire slidably disposed within the lumen of the sheath, and a locking element. The locking element may comprise a proximal end, a distal end, an intermediate region disposed between the proximal end and the distal end, and a lumen extending from the proximal end to the distal end, a first inner diameter adjacent to the distal end, a second inner diameter adjacent to the proximal end, the second inner diameter smaller than the first outer diameter, and an angled protrusion extending radially inward from an inner surface of the lumen of the locking element. A distal end region of the locking element may be configured to freely slide over the sheath. When a proximal end region of the locking element is disposed over the sheath, the locking element may be configured to depress the sheath radially inwards.

Alternatively or additionally to any of the examples above, in another example, the angled protrusion of the sheath may reduce in diameter in a proximal direction.

Alternatively or additionally to any of the examples above, in another example, the angled protrusion of the sheath may be positioned adjacent to the proximal end of the sheath.

Alternatively or additionally to any of the examples above, in another example, the angled protrusion of the locking element may reduce in diameter in a distal direction.

Alternatively or additionally to any of the examples above, in another example, the angled protrusion of the locking element may be positioned adjacent to the distal end of the locking element.

Alternatively or additionally to any of the examples above, in another example, the angled protrusion of the sheath and the angled protrusion of the locking element may be configured to cooperate to limit axial movement of the locking element.

Alternatively or additionally to any of the examples above, in another example, the lumen of the locking element within the proximal end region may reduce in diameter in a sloped manner towards the proximal end of the locking element.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
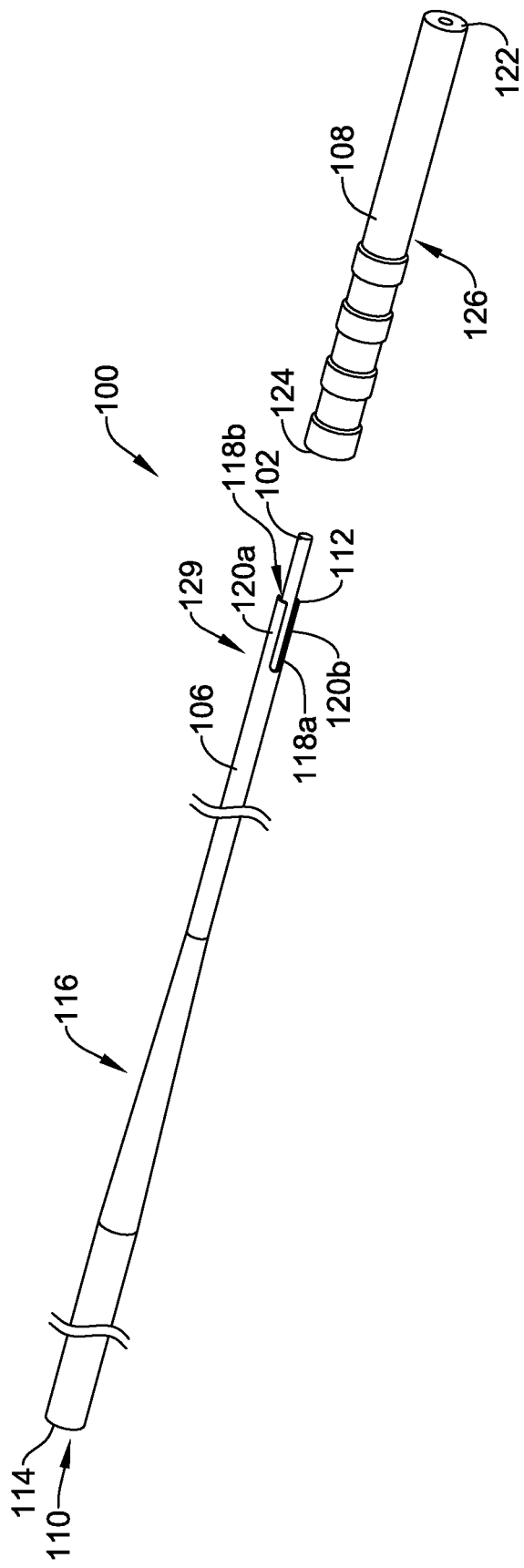
FIG. 1 is a perspective view of an example medical device system in a first configuration.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device. Still other relative terms, such as "axial", "circumferential", "longitudinal", "lateral", "radial", etc. and/or variants thereof generally refer to direction and/or orientation relative to a central longitudinal axis of the disclosed structure or device.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Diseases and/or medical conditions that impact and/or are affected by the cardiovascular system are prevalent throughout the world. For example, some forms of arterial venous malformations (AVMs) may "feed" off of normal blood flow through the vascular system. Without being bound by theory, it is believed that it may be possible to treat, at least partially, arterial venous malformations and/or other diseases or conditions by starving them of normal, oxygen and/or nutrient-rich blood flow, thereby limiting their ability to grow and/or spread. Other examples of diseases or conditions that may benefit from vascular occlusion include, but are not limited to, bleeds, aneurysms, venous insufficiency, shutting off blood flow prior to organ resection, or preventing embolic bead reflux into branch vessels in the liver. Disclosed herein are medical devices that may be used within a portion of the cardiovascular system in order to treat and/or repair some arterial venous malformations and/or other diseases or conditions. The devices disclosed herein may also provide a number of additional desirable features and benefits as described in more detail below.

FIG. 1 is a perspective view of an example medical device system 100 in a partially unassembled configuration. The medical device system 100 may include a pusher wire 102, an implant 104 (see, for example, FIG. 9), such as, but not limited to, an embolic coil, an introducer sheath 106, and a locking element 108. For simplicity, the implant 104 is described as an embolic coil, but other suitable medical devices transported, delivered, used, released, etc. in a similar manner are also contemplated, including but not limited to, vascular occlusion devices coils, stents, embolic filters, replacement heart valves, other occlusion devices, and/or other medical implants, etc.

Embolic coils 104 may be typically introduced into a blood vessel by using a microcatheter (not explicitly shown) that extends from a proximal point outside the patient's body to a distal point near the embolization site. An introducer sheath 106 containing the coil 104 can be used to carry and protect the coil 104 prior to insertion into the patient. Further, the introducer sheath 106 may be used to transfer the coil to the microcatheter and/or to assist in deploying the coil at a selected embolization site. The sheath 106 may be configured to protect the implant 104 and maintain the implant 104 in a deliverable orientation, until the implant 104 is deployed. As will be described in more detail herein, the locking element 108 may be configured to limit movement (e.g., axial and rotational) of the pusher wire 102 and implant 104 within the sheath 106 until the user is ready to advance the implant 104 out of the sheath 106.

The sheath 106 may be a tubular member including a proximal end 112, a distal end 114, and an intermediate region 116 positioned therebetween. Some suitable but non-limiting materials for the sheath 106, for example, polymer materials, composite materials, etc., are described below. The sheath 106 may define a lumen 110 extending from the proximal end 112 to the distal end 114. The pusher wire 102 and implant 104 may be slidably disposed within the lumen 110 of the sheath 106 such that the pusher wire 102 and the implant 104 are radially inwards of the sheath 106. The implant 104 may be disposed proximate the distal end 114 of the sheath 106. The pusher wire 102 may be axially slidable between an interlocked position and a released position. The pusher wire 102 may be configured to be releasably attached to the implant 104. The implant 104 may be configured to expand from a delivery configuration to a deployed configuration. The pusher wire 102 may generally be a solid wire or shaft, but may also be tubular in some embodiments. Some suitable but non-limiting materials for the pusher wire 102, for example, metallic materials, polymer materials, composite materials, etc., are described below. As will be described in more detail herein, the pusher wire 102 may be releasably secured to the sheath 106 via the locking element 108 to limit axial and/or rotational movement of the pusher wire 102 within the sheath 106.

The sheath 106 may have a first slot 118a and a second slot 118b (collectively, 118) extending distally from the proximal end 112. The first and second slots 118a, 118b may be positioned across from another or spaced approximately 180° about the circumference of the sheath 106. While the sheath 106 is described as having two slots, the sheath 106 may include fewer than two or more than two slots, as desired. The slots 118 may extend less than an entire length of the sheath 106. The slots 118 may remove material from the sheath 106 to create flexible arms or members 120a, 120b (collectively, 120). While the sheath 106 is described as having two arms 120, it should be understood the number of flexible arms may vary with the number of slots 118 and there can be fewer than two or more than two flexible arms, as desired. Further, the slots 118 may be uniformly or eccentrically distributed about a circumference of the sheath 106. The length and/or size of the slots 118 (and/or the arms 120) may vary to produce different degrees of wedging (between the locking element 108 and the pusher wire 102) and locking capabilities. It is contemplated that a proximal end region 129 of the sheath 106 may be formed from polypropylene or a material similar thereto. The durometer of the proximal end region 129 may be manipulated to produce a desired locking effect. In some cases, other portions of the sheath 106 may be formed from a same material as the proximal end region 129 while in other cases, other portions of the sheath 106 may be formed from a different material as the proximal end region 129. For example, the sheath 106 may include a polyimide distal tip (although this is not required).

Figure 2:
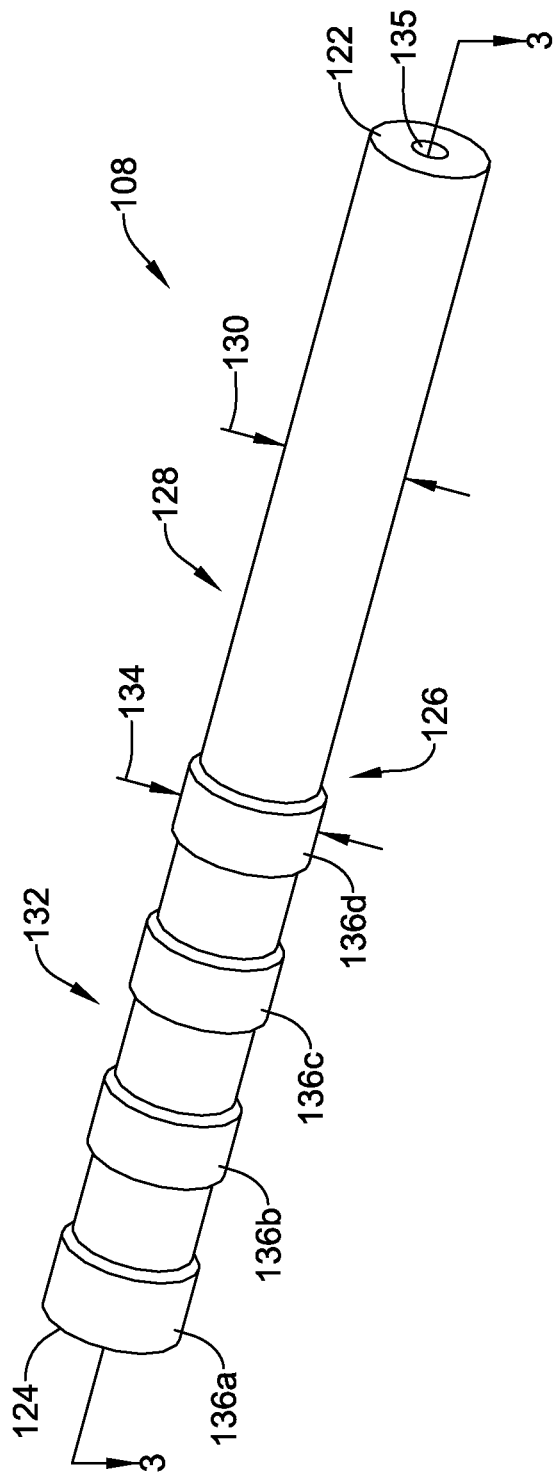
FIG. 2 is a perspective view of an illustrative locking mechanism.

Referring additionally to FIG. 2, which illustrates a perspective view of the locking element 108, the locking element 108 may be a tubular member having a proximal end 122, a distal end 124, and an intermediate region 126 positioned therebetween. The locking element 108 may have a generally constant or uniform outer diameter 130 over a proximal region 128 extending from the proximal end 122 towards and into the intermediate region 126. The locking element 108 may include a distal region 132 including plurality of raised regions or circumferential ribs 136a, 136b, 136c, 136d (collectively, 136). The circumferential ribs 136 may have an outer diameter 134 that is greater than the outer diameter 130 of the proximal region 128. It is contemplated that the circumferential ribs 136 may increase the tactility of the locking element 108 and/or make the locking element 108 easier to grip or handle. The number of circumferential ribs 136 (e.g., fewer than four or greater than four), the size of the circumferential ribs 136 (e.g., increasing or decreasing the diameter 134), the geometry of the circumferential ribs 136 (extending about less than an entire circumference, having a different shape, etc.), positioning of the circumferential ribs 136 along a length of the locking element 108, and/or the spacing of the circumferential ribs 136 can be varied to enhance or diminish the tactility or gripability of the locking element 108, as desired.

The locking element 108 may define a lumen 135 extending from the proximal end 122 to the distal end 124. As will be discussed in more detail herein, a portion of the lumen 135 of the locking element 108 may be sized to slide freely over the sheath 106 while another portion of the lumen 135 may be sized to exert a radially inward compressing force on the sheath 106, as will be described in more detail herein. Thus, in some configurations, at least a portion of the sheath 106 may be radially inward of the locking element 108.

The locking element 108 may be formed in a variety of different manners. For example, the locking element 108 may be injection molded, heat shrunk, 3-D printed, etc. The locking element 108 may be formed from a variety of different materials such as, but not limited to, hard or soft polymers, metals, composites, etc.

Figure 3:
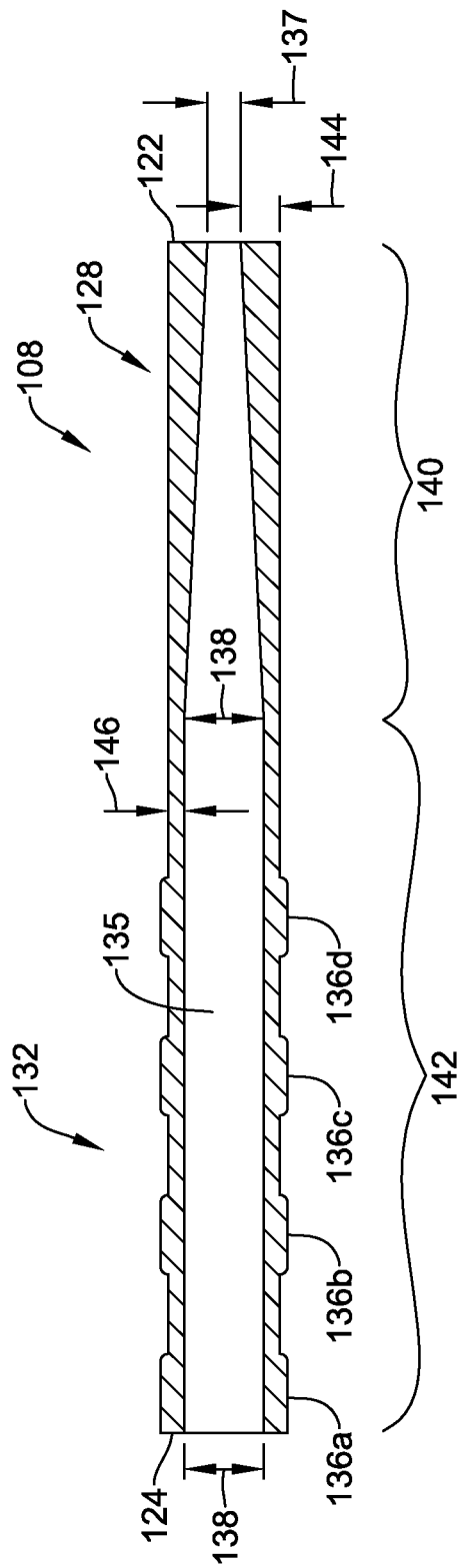
FIG. 3 is a cross-sectional view of the illustrative locking mechanism of FIG. 2.

FIG. 3 is a cross-sectional view of the locking element 108 taken at line 3-3 of FIG. 2. The locking element 108 may have a variable inner diameter. For example, in some embodiments, the locking element 108 may have an inner diameter which increases in a sloped manner over a first length 140 in the distal direction from a first inner diameter 137 adjacent the proximal end 122 to a second inner diameter 138. In some embodiments, the first length 140 may be approximately the same as a length of the arms 120 of the sheath 106, although this is not required. The second inner diameter 138 may be approximately constant or uniform over a second length 142 of the locking element 108. In some cases, while not explicitly shown, the transition from the first inner diameter 137 to the second inner diameter 138 may be an abrupt or step-wise transition. The first length 140 and/or the second length 142 may vary, as desired. Further, the slope of the first length 140 may vary, as desired. The dimensions (e.g., inner diameter, outer diameter, length, slope, etc.) of the tapered first length 140 and/or the second length 142 may be changed to create the desired locking effect (described in more detail herein).

In some embodiments, a wall thickness of the locking element 108 may vary inversely to the inner diameter over the first length 140 while the outer diameter 130 remains constant to vary the inner diameter. For example, the locking element 108 may have a wall thickness 144 adjacent the proximal end 122. The wall thickness may gradually decrease to a second wall thickness 146 at or near the second length 142. In other embodiments, the wall thickness may remain constant. In such an instance, the inner diameter and the outer diameter of the locking element 108 may vary (e.g., may be sloped in a similar manner) along the first length 140. For example, the outer diameter of the locking element 108 may increase from the proximal end 122 over the first length 140, as the inner diameter increases.

The second, larger inner diameter 138 may be sized such that the locking element 108 can slide freely over the sheath 106. The first, smaller inner diameter 137 may be sized to apply a compressive, or radially inward force on the outer surface of the sheath 106, as will be described in more detail herein.

It is contemplated that the configuration of the locking element 108 may be adjusted to create the desired effect. For example, one or more of the inner diameters 137, 138 may be made larger or smaller to accommodate different sizes of sheaths 106 and/or different outer diameters of the pusher wire 102. Further, the first and/or second lengths 140, 142 may be longer, shorter, less angled, more angled, etc. In another example, the outer diameter of the locking element 108 may be increased or decreased to facilitate handling. It is further contemplated that the outer surface of the locking element 108 may include features in addition to, or in place of the circumferential ribs 136 to improve ergonomic handling, such as, but not limited to, bumps, waves, texturing, or indentations to improve gripability. In some cases, the sheath 106 and/or the locking element 108 may include visual indicia to guide the user in manipulation of the locking element 108. In some cases, the overall length of the locking element 108 can be increased or decreased, as desired. It is further contemplated that the locking element 108 may be large enough to make it easy to handle but not so large as to be incompatible with other components, such as, but not limited to, packaging.

Figure 4:
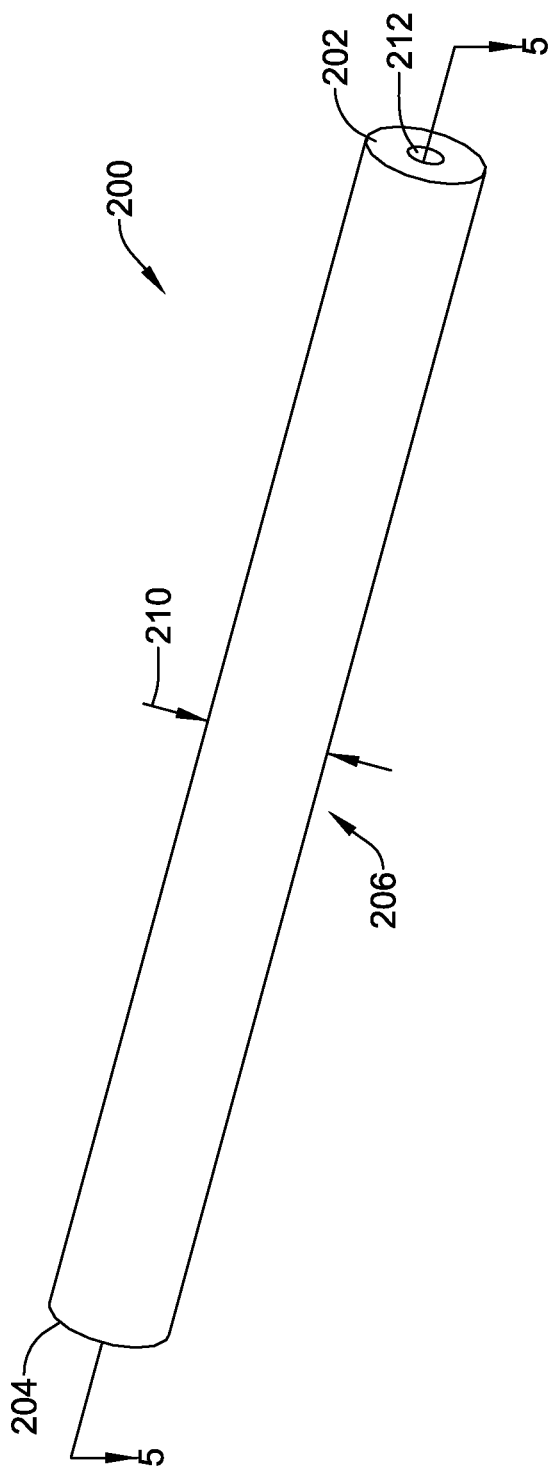
FIG. 4 is a perspective view of another illustrative locking mechanism.

FIG. 4 illustrates a perspective view of another illustrative locking element 200. The locking element 200 may be similar in form and function to the illustrative locking mechanism 108 described herein and may be used with a medical device system, such as the medical device system 100 described herein. The locking element 200 may be a tubular member having a proximal end 202, a distal end 204, and an intermediate region 206 positioned therebetween. The locking element 200 may have a generally constant or uniform outer diameter 210 extending from the proximal end 202 to the distal end 204, although this is not required. The locking element 200 may define a lumen 212 extending from the proximal end 202 to the distal end 204. As will be discussed in more detail herein, a portion of the lumen 212 of the locking element 200 may be sized to slide freely over a sheath, such as the sheath 106 described herein, while another portion of the lumen 212 may be sized to exert a radially inward or compressive force on the sheath 106, as will be described in more detail herein. Thus, in some configurations, at least a portion of the sheath 106 may be radially inward of the locking element 200.

The locking element 200 may be formed in a variety of different manners. For example, the locking element 200 may be injection molded, heat shrunk, 3-D printed, etc. The locking element 200 may be formed from a variety of different materials such as, but not limited to, hard or soft polymers, metals, composites, etc.

Figure 5:
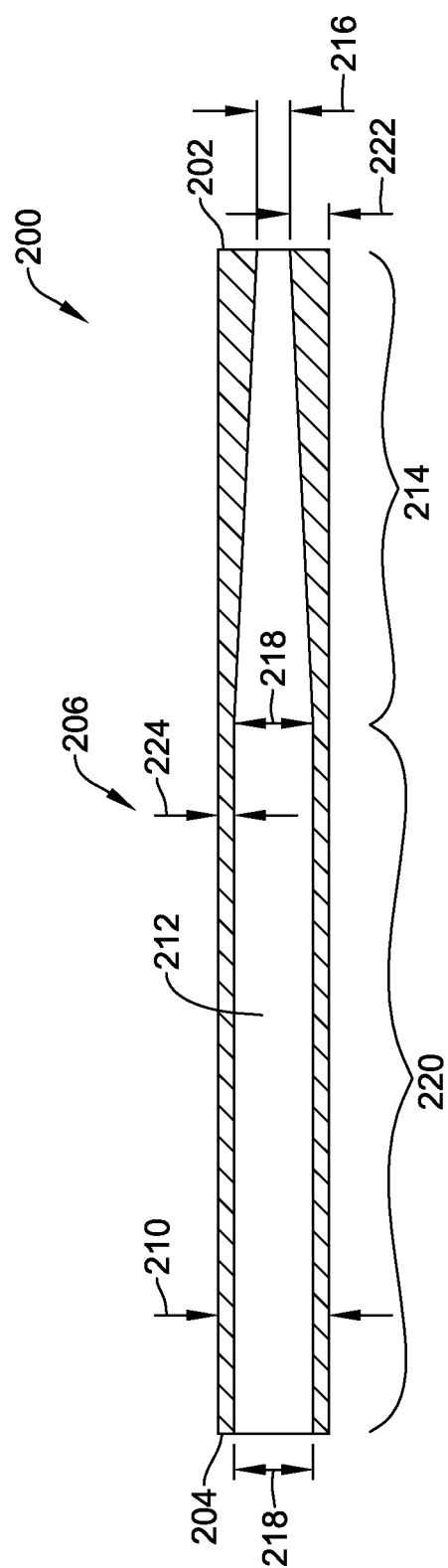
FIG. 5 is a cross-sectional view of the illustrative locking mechanism of FIG. 4.

FIG. 5 is a cross-sectional view of the locking element 200 taken at line 5-5 of FIG. 4. The locking element 200 may have a variable inner diameter. For example, in some embodiments, the locking element 200 may have an inner diameter which increases in a sloped manner over a first length 214 in the distal direction from a first inner diameter 216 adjacent the proximal end 202 to a second inner diameter 218. In some embodiments, the first length 214 may be approximately the same as a length of the arms 120 of the sheath 106, although this is not required. The second inner diameter 218 may be approximately constant or uniform over a second length 220 of the locking element 200. In some cases, while not explicitly shown, the transition from the first inner diameter 216 to the second inner diameter 218 may be an abrupt or step-wise transition. The first length 214 and/or the second length 220 may vary, as desired. Further, the slope of the first length 214 may vary, as desired. The dimensions (e.g., inner diameter, outer diameter, length, slope, etc.) of the tapered first length 214 and/or the second length 220 may be changed to create the desired locking effect (described in more detail herein).

In some embodiments, a wall thickness of the locking element 200 may vary inversely to the inner diameter over the first length 214 while the outer diameter 210 remains constant to vary the inner diameter. For example, the locking element 200 may have a first wall thickness 222 adjacent the proximal end 202. The wall thickness may gradually decrease to a second wall thickness 224 at or near the second length 220. In other embodiments, the wall thickness may remain constant. In such an instance, the inner diameter and the outer diameter of the locking element 200 may vary (e.g., may be sloped in a similar manner) along the first length 214. For example, the outer diameter of the locking element 200 may increase from the proximal end 202 over the first length 214, as the inner diameter increases.

The second, larger inner diameter 218 may be sized such that the locking element 200 can slide freely over the sheath 106. The first, smaller inner diameter 216 may be sized to apply a compressive, or radially inward force on the outer surface of the sheath 106, as will be described in more detail herein.

It is contemplated that the configuration of the locking element 200 may be adjusted to create the desired effect. For example, one or more of the inner diameters 216, 218 may be made larger or smaller to accommodate different sizes of sheaths 106. Further, the first and/or second lengths 214, 220 may be longer, shorter, less angled, more angled, etc. In another example, the outer diameter of the locking element 200 may be increased or decreased to facilitate handling. It is further contemplated that the outer surface of the locking element 200 may include features to improve ergonomic handling, such as, but not limited to, bumps, waves, texturing, or indentations to improve gripability. In some cases, the sheath 106 and/or the locking element 200 may include visual indicia to guide the user in manipulation of the locking element 200. In some cases, the overall length of the locking element 200 can be increased or decreased, as desired. It is further contemplated that the locking element 200 may be large enough to make it easy to handle but not so large as to be incompatible with other components, such as, but not limited to packaging.

Figure 6:
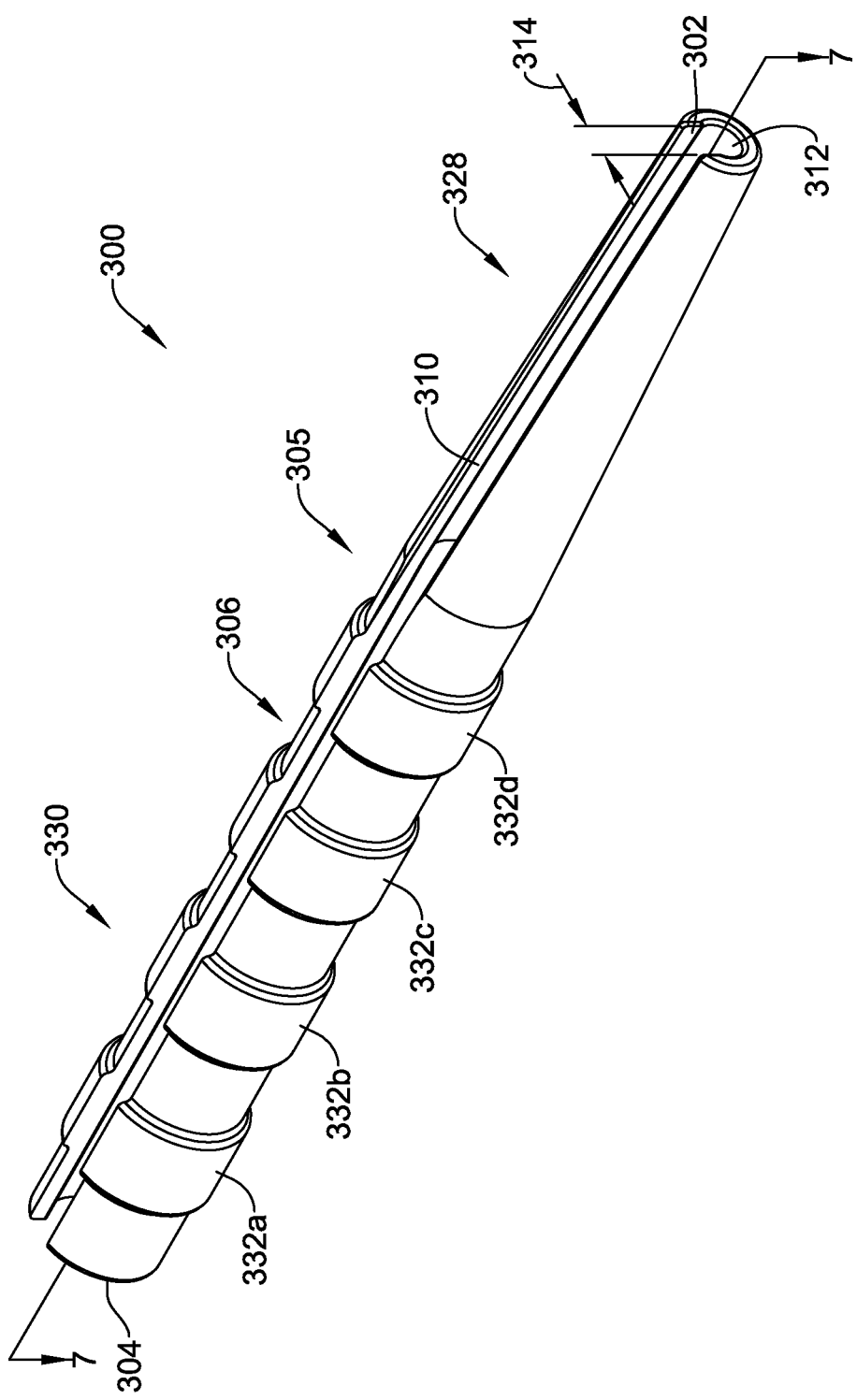
FIG. 6 is a perspective view of another illustrative locking mechanism.

FIG. 6 illustrates a perspective view of another illustrative locking element 300. The locking element 300 may be similar in form and function to the illustrative locking mechanism 108 described herein and may be used with a medical device system, such as the medical device system 100 described herein. The locking element 300 may be a tubular member having a proximal end 302, a distal end 304, and an intermediate region 305 positioned therebetween. The locking element 300 may define a lumen 312 extending from the proximal end 302 to the distal end 304. As will be discussed in more detail herein, a portion of the lumen 312 of the locking element 300 may be sized to slide freely over a sheath, such as the sheath 106 described herein, while another portion of the lumen 312 may be sized to exert a radially inward or compressive force on the sheath 106, as will be described in more detail herein. Thus, in some configurations, at least a portion of the sheath 106 may be radially inward of the locking element 300. The locking element 300 may further include a slot 310 extending from the proximal end 302 to the distal end 304. The slot 310 may extend through a thickness of the side wall of the locking element 300 (e.g., from an outer surface to an inner surface thereof). The slot 310 may have a width 314 that is greater than a width of a pusher wire (e.g., such as the pusher wire 102 described herein) but less than a width of the sheath 106. This may allow the locking element 300 to be more easily removed from the medical device system 100 as will be described in more detail herein.

The locking element 300 may have a tapered or sloped outer diameter over a proximal region 328 extending from the proximal end 302 towards and into the intermediate region 305. The locking element 300 may include a distal region 330 including plurality of raised regions or circumferential ribs 332a, 332b, 332c, 332d (collectively, 332). The circumferential ribs 332 may have an outer diameter 334 that is greater than an outer diameter 324, 326 of the proximal region 328. The circumferential ribs 332 may extend about an entire perimeter of the locking element 300, which may be less than 360° due to the slot 310. It is contemplated that the circumferential ribs 332 may increase the tactility of the locking element 300 and/or make the locking element 300 easier to grip or handle. The number of circumferential ribs 332 (e.g., fewer than four or greater than four), the size of the circumferential ribs 332 (e.g., increasing or decreasing the diameter 334), the geometry of the circumferential ribs 332 (extending about less than an entire perimeter, having a different shape, etc.), and/or the spacing of the circumferential ribs 332 can be varied to enhance or diminish the tactility or gripability of the locking element 300, as desired.

The locking element 300 may be formed in a variety of different manners. For example, the locking element 300 may be injection molded, heat shrunk, 3-D printed, etc. The locking element 300 may be formed from a variety of different materials such as, but not limited to, hard or soft polymers, metals, composites, etc.

Figure 7:
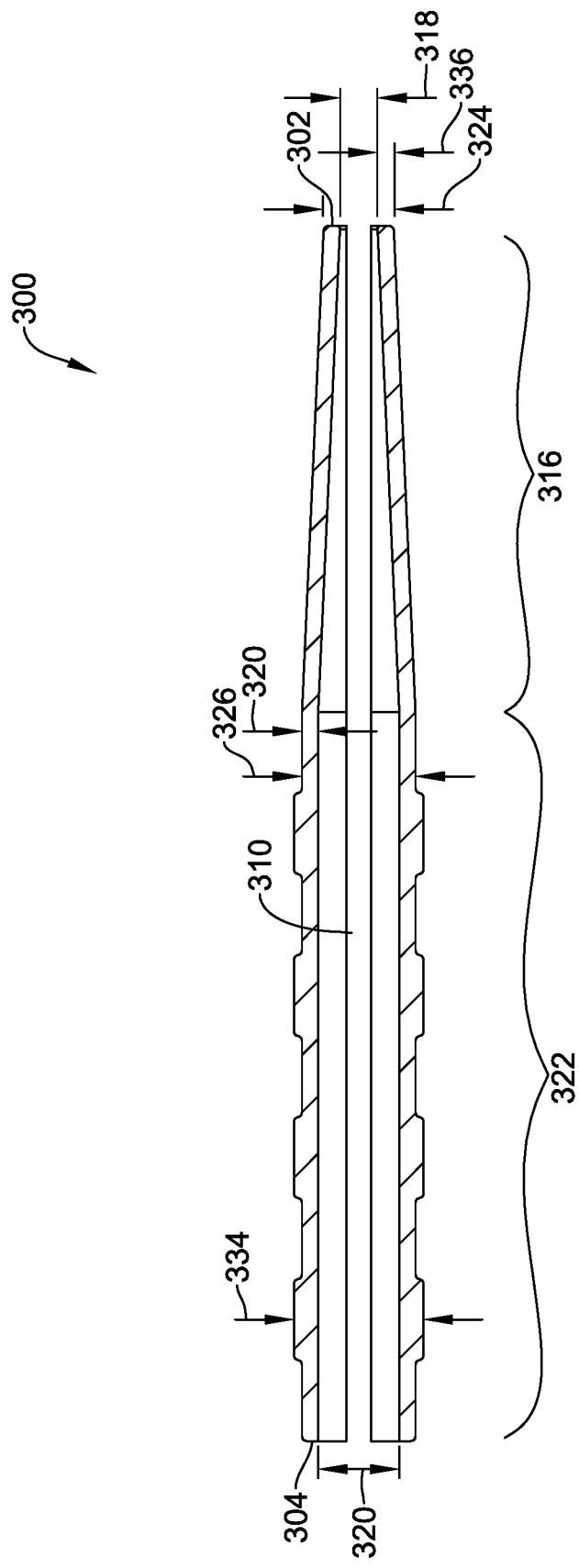
FIG. 7 is a cross-sectional view of the illustrative locking mechanism of FIG. 6.

FIG. 7 is a cross-sectional view of the locking element 300 taken at line 7-7 of FIG. 6. The locking element 300 may have a variable outer diameter and a variable inner diameter. For example, in some embodiments, the locking element 300 may have an inner diameter which increases in a sloped manner over a first length 316 in the distal direction from a first inner diameter 318 adjacent the proximal end 302 to a second inner diameter 320. In some embodiments, the first length 316 may be approximately the same as a length of the arms 120 of the sheath 106, although this is not required. The second inner diameter 320 may be approximately constant or uniform over a second length 322 of the locking element 300. In some cases, while not explicitly shown, the transition from the first inner diameter 318 to the second inner diameter 320 may be an abrupt or step-wise transition. The first length 316 and/or the second length 322 may vary, as desired. Further, the slope of the first length 316 may vary, as desired. The second, larger inner diameter 320 may be sized such that the locking element 300 can slide freely over the sheath 106. The first, smaller inner diameter 318 may be sized to apply a compressive, or radially inward force on the outer surface of the sheath 106, as will be described in more detail herein.

In some embodiments, a wall thickness 336 of the locking element 300 may remain generally uniform over the first and/or second lengths 316, 322 of the locking element 300. In such an instance, the inner diameter and the outer diameter of the locking element 300 may vary (e.g., may be sloped in a similar manner) along the first length 316. For example, the outer diameter of the locking element 300 may increase from a first outer diameter 324 at the proximal end 302 to a second outer diameter 326 (greater than the first outer diameter 324) over the first length 316, as the inner diameter increases. In some embodiments, the wall thickness 336 may vary over the first and/or second lengths 316, 322 of the locking element 300. For example, when circumferential ribs 332 are provided, the wall thickness adjacent the ribs 332 may be greater than the wall thickness 336 of other portions of the locking element 300. In other embodiments, the wall thickness 336 may vary to vary the diameter of the lumen 310.

It is contemplated that the configuration of the locking element 300 may be adjusted to create the desired effect. The dimensions (e.g., inner diameter, outer diameter, length, slope, etc.) of the tapered first length 316 and/or the second length 322 may be changed to create the desired locking effect (described in more detail herein). For example, one or more of the inner diameters 318, 320 may be made larger or smaller to accommodate different sizes of sheaths 106. Further, the first and/or second lengths 316, 322 may be longer, shorter, less angled, more angled, etc. In another example, the outer diameter of the locking element 300 may be increased or decreased to facilitate handling. It is further contemplated that the outer surface of the locking element 300 may include features to improve ergonomic handling, such as, but not limited to, bumps, waves, texturing, or indentations to improve gripability. In some cases, the sheath 106 and/or the locking element 300 may include visual indicia to guide the user in manipulation of the locking element 300. In some cases, the overall length of the locking element 300 can be increased or decreased, as desired. It is further contemplated that the locking element 300 may be large enough to make it easy to handle but not so large as to be incompatible with other components, such as, but not limited to packaging.

Figure 8:
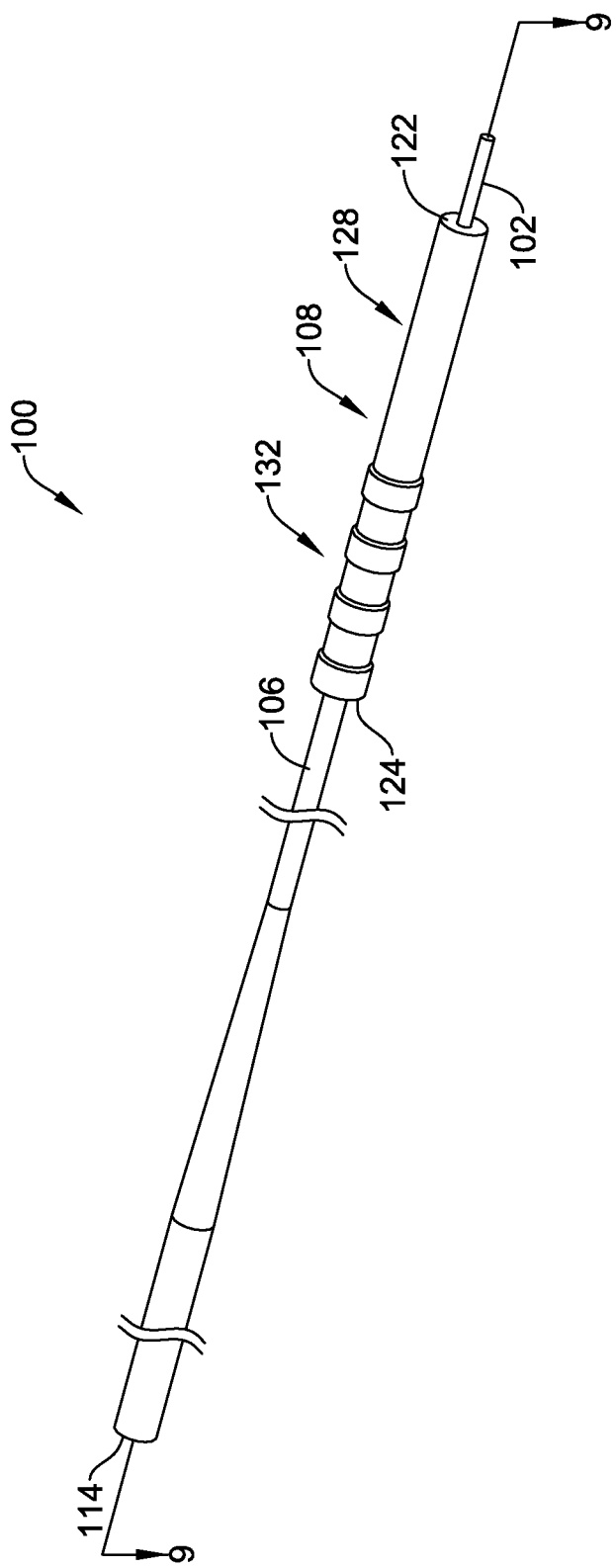
FIG. 8 is a perspective view of the illustrative medical device system of FIG. 1 in a second configuration.
Figure 9:
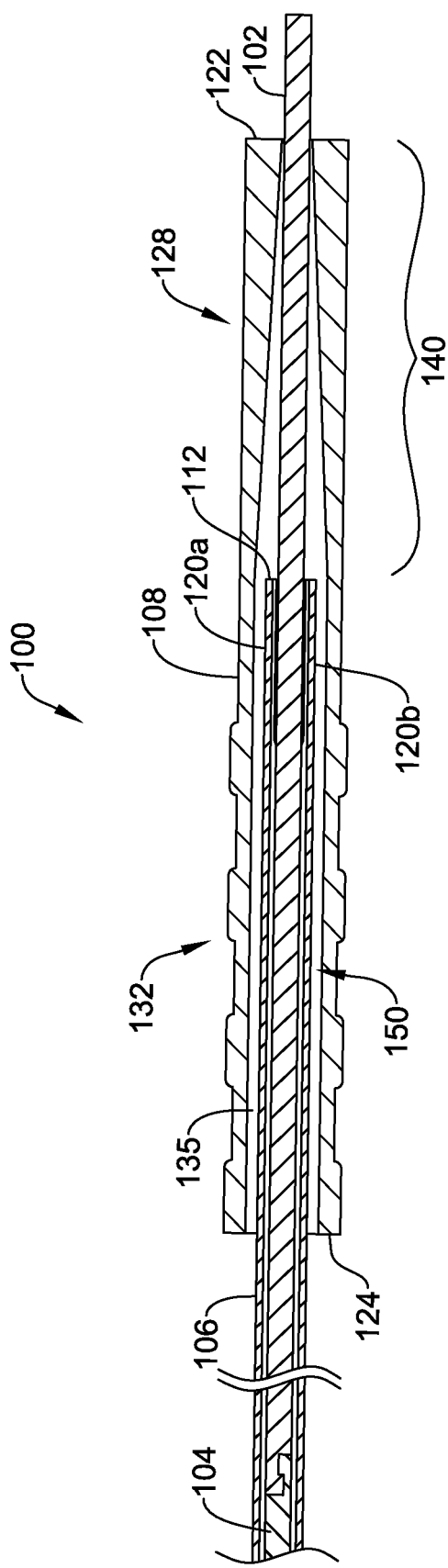
FIG. 9 is a partial cross-sectional view of the illustrative medical device system of FIG. 8.

FIG. 8 is a perspective view of the illustrative medical device system 100 in an unlocked or first assembled configuration and FIG. 9 is a partial cross-sectional view of the illustrative medical device system 100, taken at line 9-9 of FIG. 8. While the medical device system 100 is described with respect to a particular locking element 108, it should be understood that any of the locking elements described herein, including but not limited to, the locking elements 200, 300, 408, 508, 600, 708, 800, may be substituted for the locking element 108. From the partially unassembled configuration illustrated in FIG. 1, to position the locking element 108 such that it can be used to secure the pusher wire 102, the locking element 108 is distally advanced over a proximal end region 129 of the sheath 106 from the proximal end 112. An entirety of the locking element 108 may not be disposed over sheath 106 in the first assembled configuration. For example, the first length 140 of the locking element 108 having the reduced inner diameter may be only partially disposed over the sheath 106 or not over the sheath 106 at all. In this configuration, the pusher wire 102 is free to slide axially (e.g., proximally and distally) and/or rotate within the lumen 110 of the sheath 106. As described above, the inner diameter of the sheath 106 may remain constant, or substantially constant from the proximal end 112 to the distal end 114.

Figure 10:
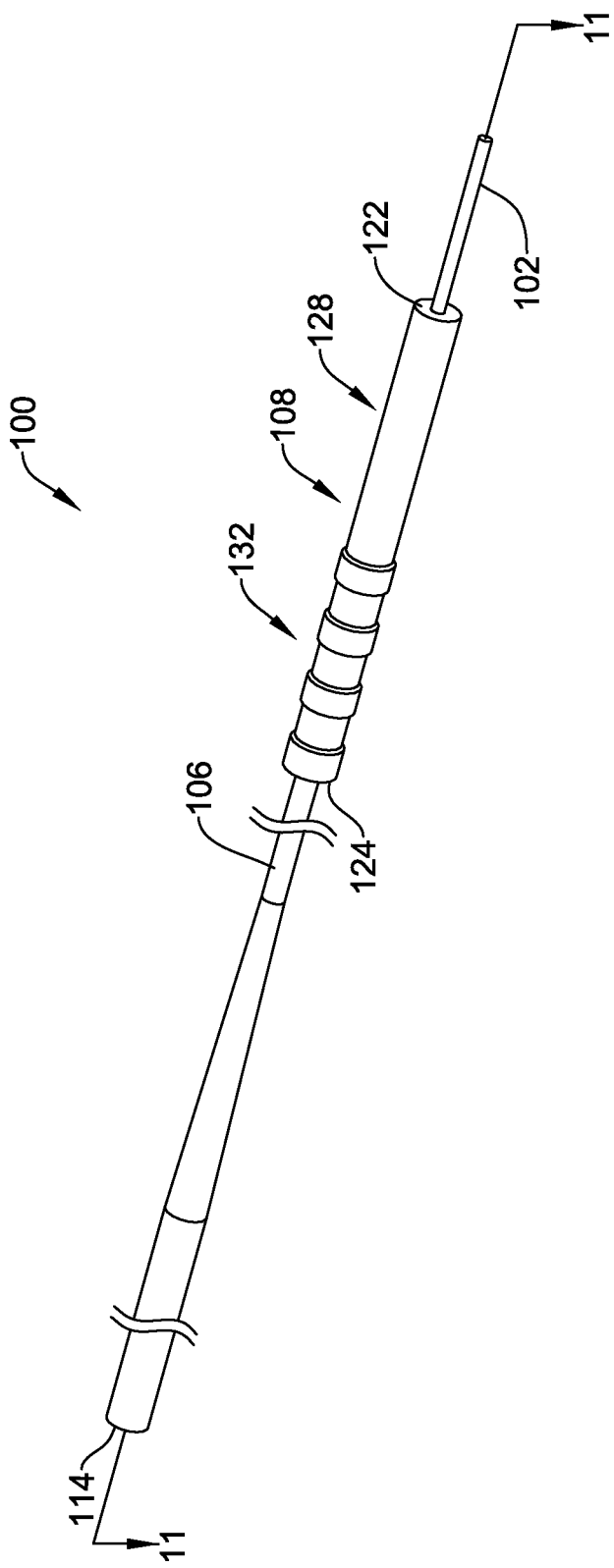
FIG. 10 is a perspective view of the illustrative medical device system of FIGS. 1 and 8 in a third configuration.
Figure 11:
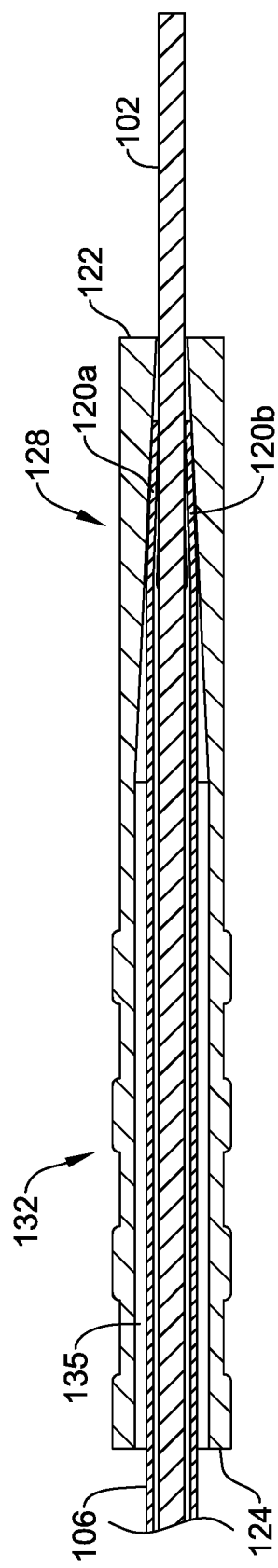
FIG. 11 is a partial cross-sectional view of the illustrative medical device system of FIG. 10.

To lock the pusher wire 102 relative to the sheath 106, the locking element 108 is advanced further in the distal direction until the first length 140 of the locking element 108 is disposed over the arms 120 of the sheath 106. FIG. 10 is a perspective view of the illustrative medical device system 100 in a locked or second assembled configuration and FIG. 11 is a partial cross-sectional view of the illustrative medical device system 100, taken at line 11-11 of FIG. 10. As described above, the distal portion 132 and a portion of the proximal portion 128 of locking element 108 may slide freely over the proximal end region 129 of the sheath. When proximal portion 128 having the reduced diameter of the locking element 108 reaches the outer sheath 106, the arms 120 of the sheath 106 may be depressed onto an outer surface of the pusher wire 102. For example, the locking element 108 may freely slide over the outer sheath 106 until the inner diameter of the locking element 108 is approximately equal to or less than an outer diameter of the sheath 106. It is contemplated that the wall thickness of the outer sheath 106 and the outer diameter of the pusher wire 102 may collectively affect how much the sheath arms 120 collapse before locking on the pusher wire 102. Once the inner diameter of the locking element 108 begins to frictionally engage the outer surface of the sheath 106 more force may be required to continue distal movement of the locking element 108. As the locking element 108 is distally advanced further onto the sheath 106, the tapered region (e.g., the first length 140) acts to deflect the arms 120 of the sheath 106 inward and onto the wire 102. When advanced far enough, the locking element 108 wedges in place, creating the desired locking effect between the sheath 106 and the pusher wire 102. For example, the tapered portion of the lumen 135 of the locking element 108 may act as a wedge to pinch or exert a radially inward biasing force on an outer surface of the arms 120 of the sheath 106 such that the outer diameter of the arms 120 is decreased and the inner diameter of the arms is biased radially inward, as shown in FIG. 11. As the inner diameter of the arms 120 is reduced, the inner surface of the arms 120 contacts and frictionally engages an outer surface of the pusher wire 102.

In the locked configuration illustrated in FIGS. 10 and 11, the frictional engagement between the inner surface of the sheath 106 and the outer surface of the pusher wire 102 may preclude or inhibit axial (e.g., proximally and distally) and/or rotational movement of the pusher wire 102 within the lumen 110 of the sheath 106. In some embodiments, the arms 120 are configured to promote inward deflection thereof. For example, the cut pattern of the slots 118 may be applied to promote collapse of the arms 120 and to create a localized friction point between an inner surface of the sheath 106 (e.g., the inner surface of the arms 120) and the pusher wire 102.

It is contemplated that the gradual decrease in the inner diameter of the locking element 108 may facilitate positioning of the locking element 108 over the sheath 106. For example, the inner diameter 138 of the locking element 108 at the distal portion 132 (and/or portions of the proximal portion 128 may be large enough to freely pass over the outer diameter of the sheath 106. As the inner diameter of the locking element tapers (e.g., in the proximal direction towards the proximal end 122) to a dimension smaller than the outer diameter of the sheath 106, and is distally advanced far enough over the sheath 106, it promotes collapse of the arms 120. This creates a friction lock between the sheath 106 and pusher wire 102 when the pusher wire 102 is positioned through the sheath 106.

When the user is ready to advance the implant 104, the locking element 108 may be removed proximally from the proximal region 129 of the sheath 106. This may allow the inner diameter of the sheath 106 adjacent to the arms 120 to expand to the original configuration thus removing the friction lock and allowing the pusher wire 102 to move freely. Thus, as the sheath 106 is removed from the pusher wire 102 and/or the pusher wire 102 is distally advanced, the sheath 106 does not engage or hang up on any portion of the pusher wire 102.

It is contemplated that when the locking element 108 is provided with a longitudinally extending slot, such as the slot 310 illustrated in the locking element 300, the locking element 108 may be free to drop off of the pusher wire 102 (e.g., via the slot) without having to be proximally retracted over an entirety of the length of the pusher wire 102 proximal to the sheath 106. Similarly, during loading of the locking element 108 at the time of manufacture, the locking element 108 can be placed over the pusher wire 102 rather than threading the locking element 108 over the pusher wire 102. As described above with respect to FIGS. 6 and 7, if so provided a longitudinal slot may be sized such that the pusher wire 102 can fit through the slot, but not the sheath 106. This may ensure the locking element 108 does not fall off the sheath 106 in the locked position (e.g., FIGS. 10 and 11) but can be easily removed from the pusher wire 102 once the locking element is in the unlocked configuration.

It is further contemplated that that locking element 108 may be formed from a material that is more rigid than or stiffer than the outer sheath 106. For example, the material for the locking element 108 may be selected such that the locking element 108 does not deflect when the tapered portion of the lumen 135 of the locking element 108 is advanced over the sheath 106 but rather forces the sheath 106 to deflect inward. In some embodiments, the locking element 108 may be formed from a bright (or other) color easily noticeable by the user.

Figure 12:
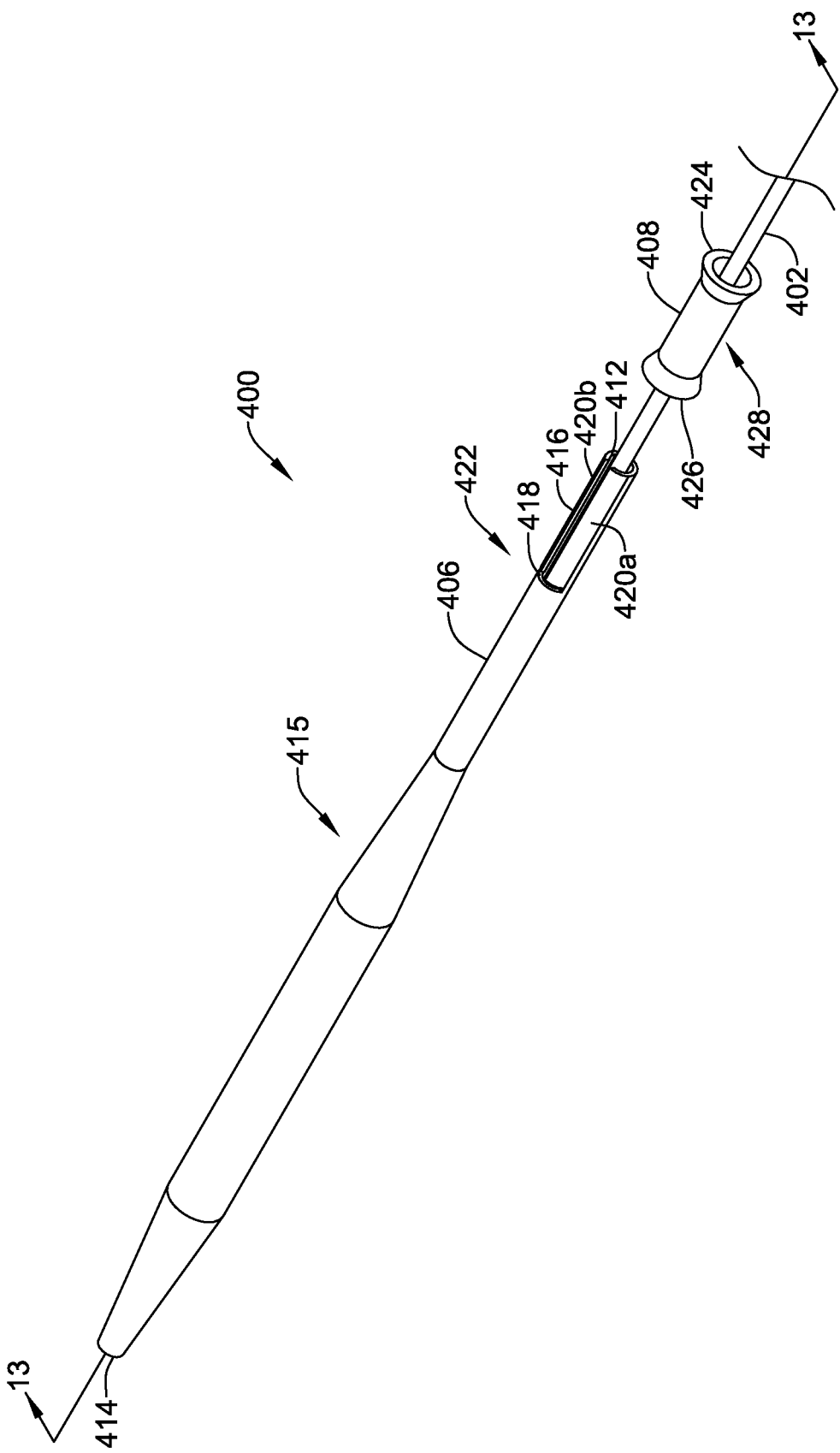
FIG. 12 is a perspective view of another example medical device system in a first configuration.
Figure 13:
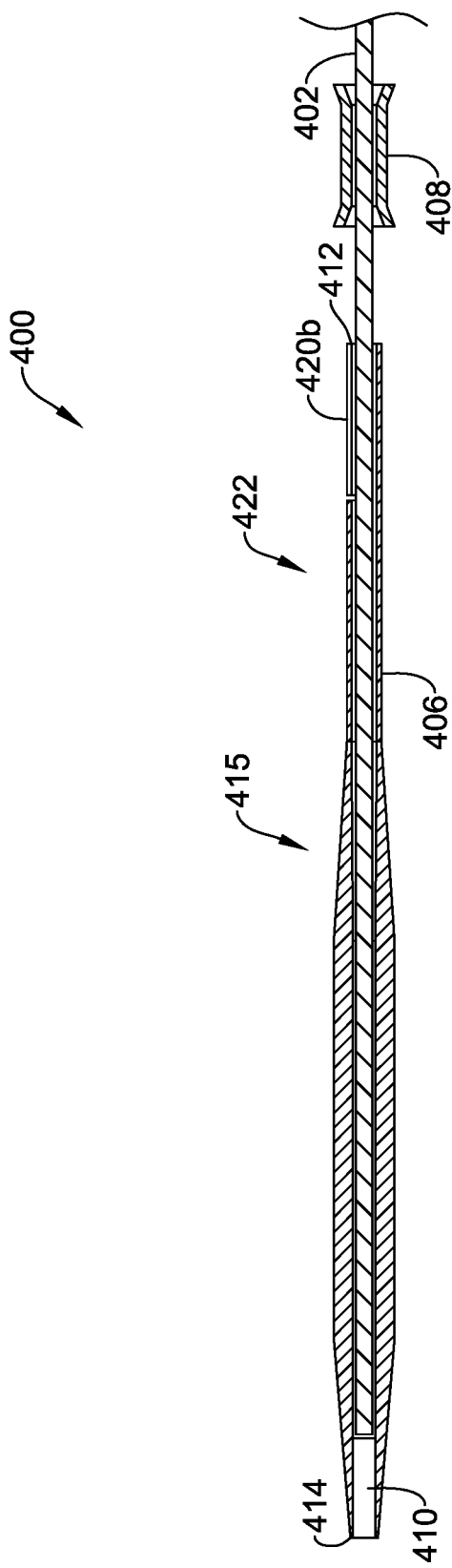
FIG. 13 is a partial cross-sectional view of the illustrative medical device system of FIG. 12.

FIG. 12 is a perspective view of another illustrative medical device system 400 in a partially unassembled configuration. FIG. 13 is a cross-sectional view of the illustrative medical device system 400 taken at line 13-13 of FIG. 12. The medical device system 400 may include a pusher wire 402, an implant (not explicitly shown), such as, but not limited to, an embolic coil, an introducer sheath 406, and a locking element 408. For simplicity, the implant is described as an embolic coil, but other suitable medical devices transported, delivered, used, released, etc. in a similar manner are also contemplated, including but not limited to, vascular occlusion devices coils, stents, embolic filters, replacement heart valves, other occlusion devices, and/or other medical implants, etc.

Embolic coils may be typically introduced into a blood vessel by using a microcatheter (not explicitly shown) that extends from a proximal point outside the patient's body to a distal point near the embolization site. An introducer sheath 406 containing the coil can be used to carry and protect the coil prior to insertion into the patient. Further, the introducer sheath 406 may be used to transfer the coil to the microcatheter and/or to assist in deploying the coil at a selected embolization site. The sheath 406 may be configured to protect the implant and maintain the implant in a deliverable orientation, until the implant is deployed. As will be described in more detail herein, the locking element 408 may be configured to limit movement (e.g., axial and rotational) of the pusher wire 402 and implant within the sheath 406 until the user is ready to advance the implant out of the sheath 406.

The sheath 406 may be a tubular member including a proximal end 412, a distal end 414, and an intermediate region 415 positioned therebetween. Some suitable but non-limiting materials for the sheath 406, for example, polymer materials, composite materials, etc., are described below. The sheath 406 may define a lumen 410 extending from the proximal end 412 to the distal end 414. The pusher wire 402 and implant may be slidably disposed within the lumen 410 of the sheath 406 such that the pusher wire 402 and the implant are radially inwards of the sheath 406. The implant may be disposed proximate the distal end 414 of the sheath 406. The pusher wire 402 may be axially slidable between an interlocked position and a released position. The pusher wire 402 may be configured to be releasably attached to the implant. The implant may be configured to expand from a delivery configuration to a deployed configuration. The pusher wire 402 may generally be a solid wire or shaft, but may also be tubular in some embodiments. Some suitable but non-limiting materials for the pusher wire 402, for example metallic materials, polymer materials, composite materials, etc., are described below. As will be described in more detail herein, the pusher wire 402 may be releasably secured to the sheath 406 via the locking element 408 to limit axial and/or rotational movement of the pusher wire 402 within the sheath 406.

The sheath 406 may have a longitudinally extending slot 416 extending distally from the proximal end 412. The slot 416 may terminate at a "C" cut 418 extending about a circumference of the sheath 416. The cut 418 may be positioned in a plane that is generally perpendicular to the longitudinal axis of the sheath 406. In some cases, the cut 418 may extend less than 360°, less than 270°, less than 180°, less than 135°, less than 90° about the circumference of the sheath 406, as desired. It is contemplated that the radial length of the cut 418 may be varied to produce a desired locking effect. Similarly, the length and width of the slot 416 may be varied to produce a desired locking effect. The slot 416 and the cut 418 may allow the free edges or flaps 420a, 420b (collectively, 420) of the sheath 406 to fold over or collapse when a radially inward force is applied to an outer surface thereof to create a frictional lock, as will be described in more detail here.

It is contemplated that a proximal end region 422 of the sheath 406 may be formed from polypropylene or a material similar thereto. The durometer of the proximal end region 422 may be manipulated to produce a desired locking effect. In some cases, other portions of the sheath 406 may be formed from a same material as the proximal end region 422 while in other cases, other portions of the sheath 406 may be formed from a different material as the proximal end region 422. For example, the sheath 406 may include a polyimide distal tip (although this is not required).

Figure 14:
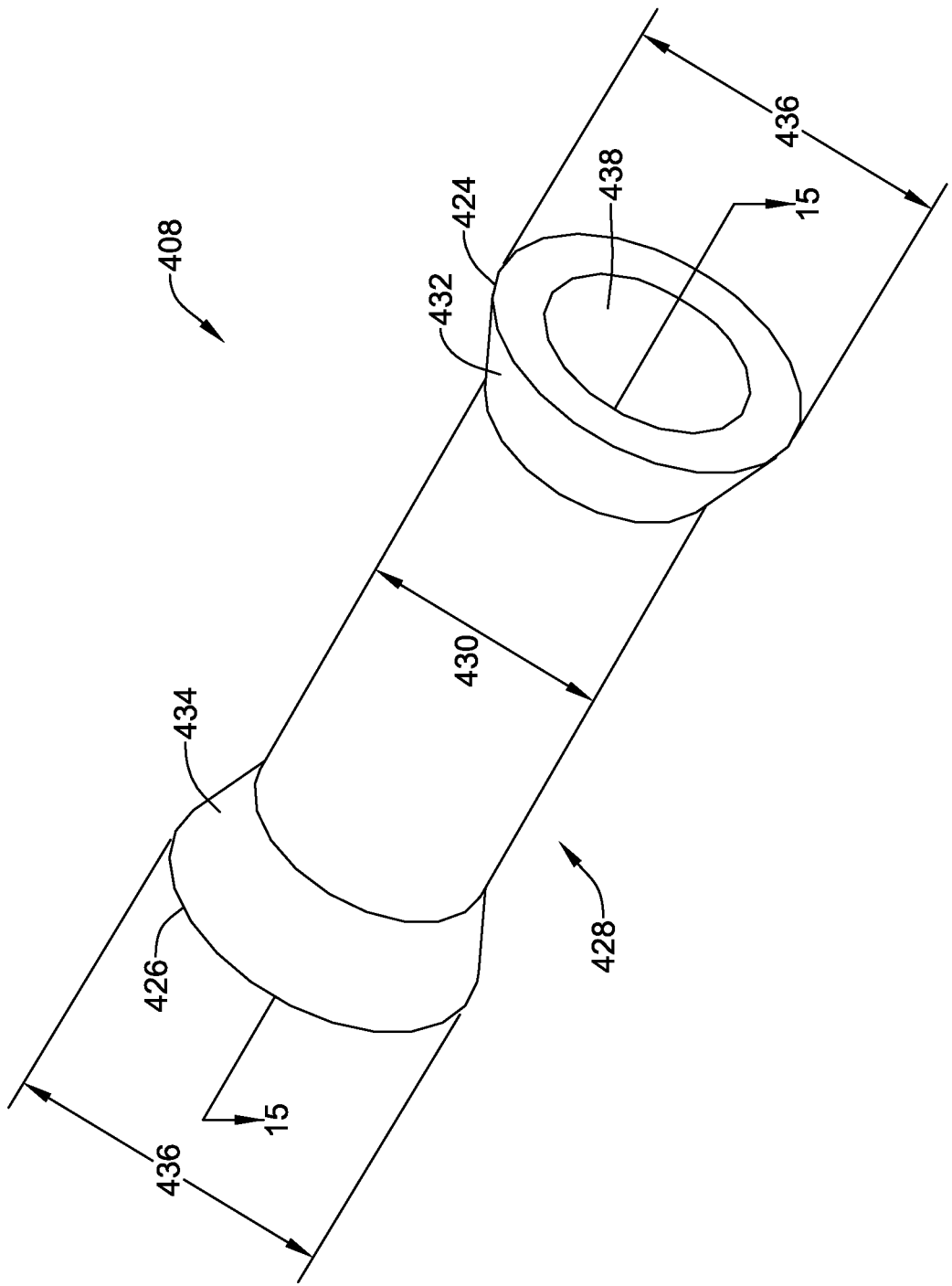
FIG. 14 is a perspective view of another illustrative locking mechanism.

Referring additionally to FIG. 14, which illustrates a perspective view of the locking element 408, the locking element 408 may be a tubular member having a proximal end 424, a distal end 426, and an intermediate region 428 positioned therebetween. The locking element 408 may have a generally constant or uniform outer diameter 430 over the intermediate region 428. The outer diameter may increase from the intermediate region 428 in both the proximal and distal directions to create a flared proximal portion 432 and a flared distal portion 434. The flared proximal portion 432 may increase in diameter towards the proximal end 424 to a second outer diameter 436 greater than the first outer diameter 430 adjacent to the intermediate region 428. Similarly, the flared distal portion 434 may increase in diameter towards the distal end 426 to the second outer diameter 436 greater than the first outer diameter 430 adjacent to the intermediate region 428.

The locking element 408 may define a lumen 438 extending from the proximal end 424 to the distal end 426. As will be discussed in more detail herein, a portion of the lumen 438 of the locking element 408 may be sized to slide freely over the sheath 406 while another portion of the lumen 438 may be sized to exert a radially inward compressing force on the sheath 406, as will be described in more detail herein. Thus, in some configurations, at least a portion of the sheath 406 may be radially inward of the locking element 408.

The locking element 408 may be formed in a variety of different manners. For example, the locking element 408 may be injection molded, heat shrunk, 3-D printed, etc. The locking element 408 may be formed from a variety of different materials such as, but not limited to, hard or soft polymers, metals, composites, etc.

Figure 15:
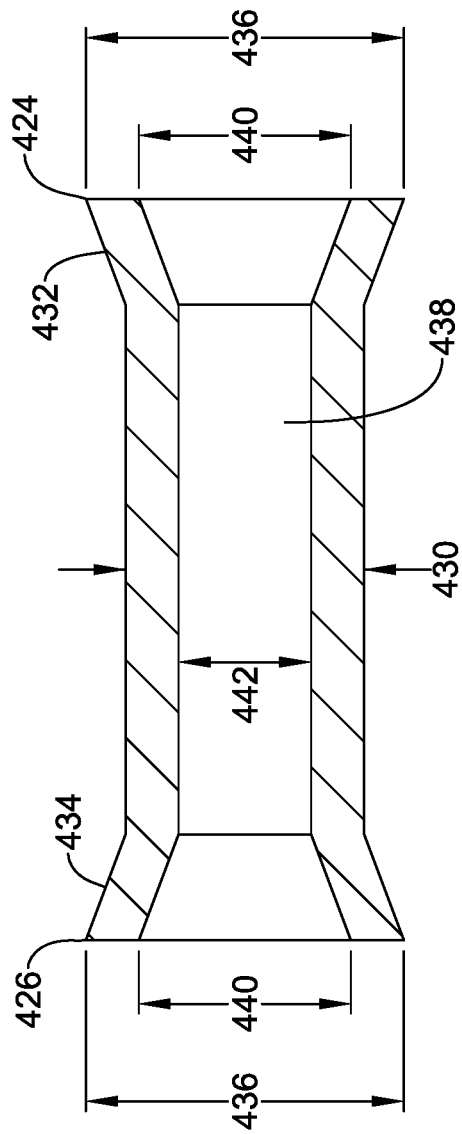
FIG. 15 is a cross-sectional view of the illustrative locking mechanism of FIG. 14.

FIG. 15 is a cross-sectional view of the locking element 408 taken at line 15-15 of FIG. 14. The locking element 408 may have a variable inner diameter. In some cases, the lumen 438 may have a generally hourglass shape. For example, in some embodiments, the locking element 408 may have an inner diameter which has a first inner diameter 440 adjacent to the proximal and distal ends 424, 426 thereof. The first inner diameter 440 may taper or slope towards a second generally constant inner diameter 442. It is contemplated that the sloped inner diameter may generally correspond to the flared proximal and distal portions 432, 434 while the generally constant inner diameter 442 may generally correspond to the intermediate region 428. However, this is not required. However, in such an arrangement, the locking element 408 may have a generally uniform wall thickness from the proximal end 424 to the distal end 426 thereof. In other embodiments the inner diameter of the locking element 408 may be varied by varying a wall thickness of the locking element 408 along a length thereof. Further, in some cases, while not explicitly shown, the transition from the first inner diameter 440 to the second inner diameter 442 may be an abrupt or step-wise transition. The dimensions (e.g., inner diameter, outer diameter, length, slope, etc.) of the flared proximal portion 432, the flared distal portion 434 and/or the intermediate region 428 may be changed to create the desired locking effect (described in more detail herein).

The first, larger inner diameter 440 may be sized such that the locking element 408 can slide freely over the sheath 406. The first, smaller inner diameter 442 may be sized to apply a compressive, or radially inward force on the outer surface of the sheath 406, as will be described in more detail herein.

It is contemplated that the configuration of the locking element 408 may be adjusted to create the desired effect. For example, one or more of the inner diameters 440, 442 may be made larger or smaller to accommodate different sizes of sheaths 406. Further, the flared proximal portion 432, the flared distal portion 434 and/or the intermediate region 428 may be longer, shorter, less angled, more angled, etc. In another example, the outer diameter of the locking element 408 may be increased or decreased to facilitate handling. It is further contemplated that the outer surface of the locking element 408 may include features to improve ergonomic handling, such as, but not limited to, bumps, waves, texturing, or indentations to improve gripability. In some cases, the sheath 406 and/or the locking element 408 may include visual indicia to guide the user in manipulation of the locking element 408. In some cases, the overall length of the locking element 408 can be increased or decreased, as desired. It is further contemplated that the locking element 408 may be large enough to make it easy to handle but not so large as to be incompatible with other components, such as, but not limited to packaging.

Figure 16:
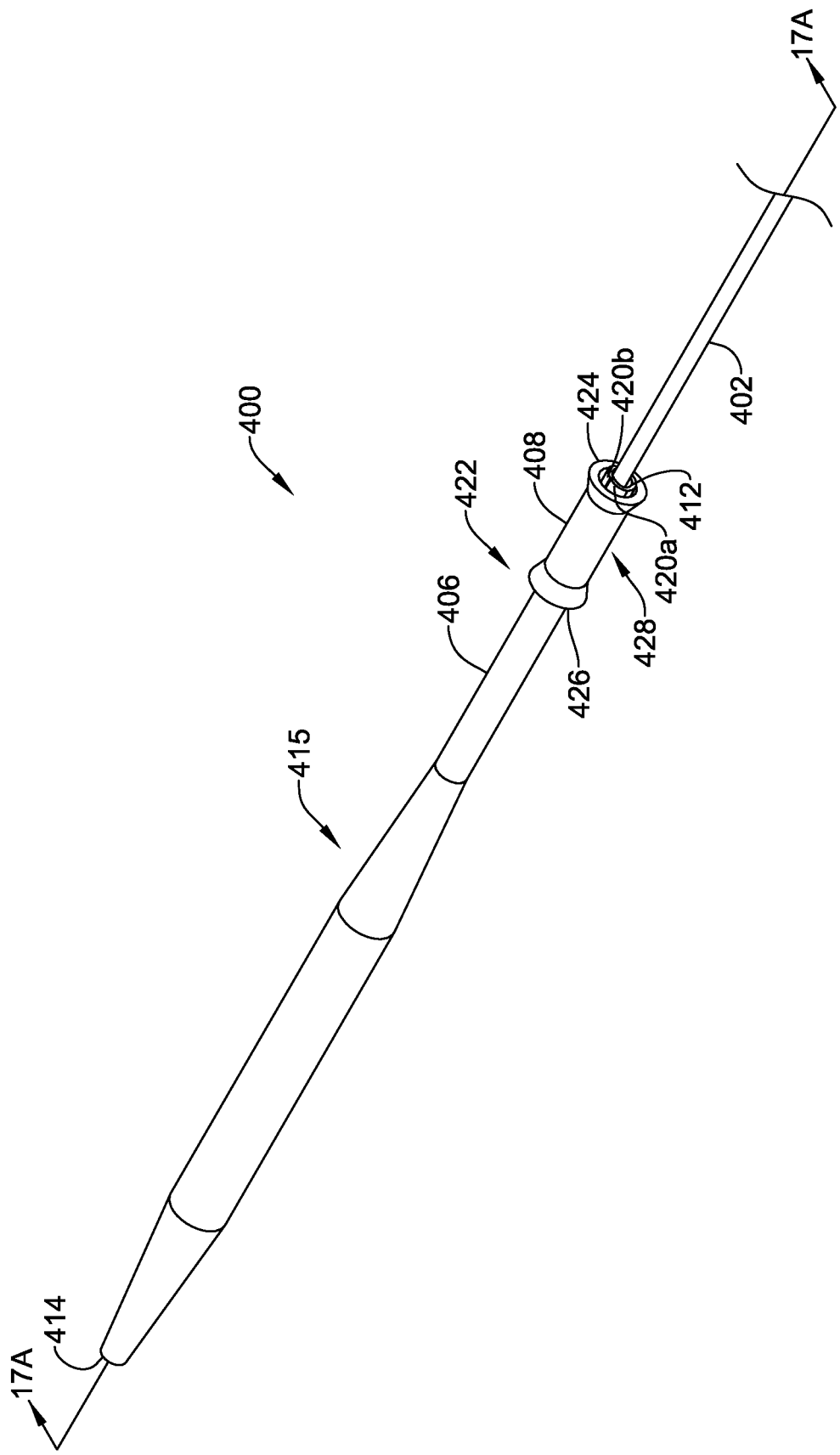
FIG. 16 is a perspective view of the illustrative medical device system of FIG. 12 in a second configuration.
Figure 17A:
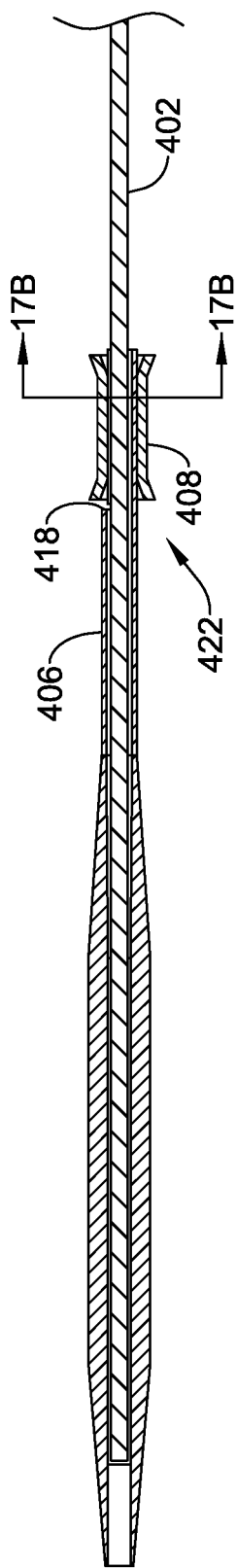
FIG. 17A is a partial cross-sectional view of the illustrative medical device system of FIG. 16.

FIG. 16 is a perspective view of the illustrative medical device system 400 in a locked configuration and FIG. 17A is a partial cross-sectional view of the illustrative medical device system 400, taken at line 17A-17A of FIG. 16. While the medical device system 400 is described with respect to a particular locking element 408, it should be understood that any of the locking elements described herein, including but not limited to the locking elements 108, 200, 300, 508, 600, 708, 800, may be substituted for the locking element 408. From the partially unassembled configuration illustrated in FIG. 12, to position the locking element 408 such that it can be used to secure the pusher wire 402, the locking element 408 is distally advanced over a proximal end region 422 of the sheath 406 from the proximal end 412.

Figure 17B:
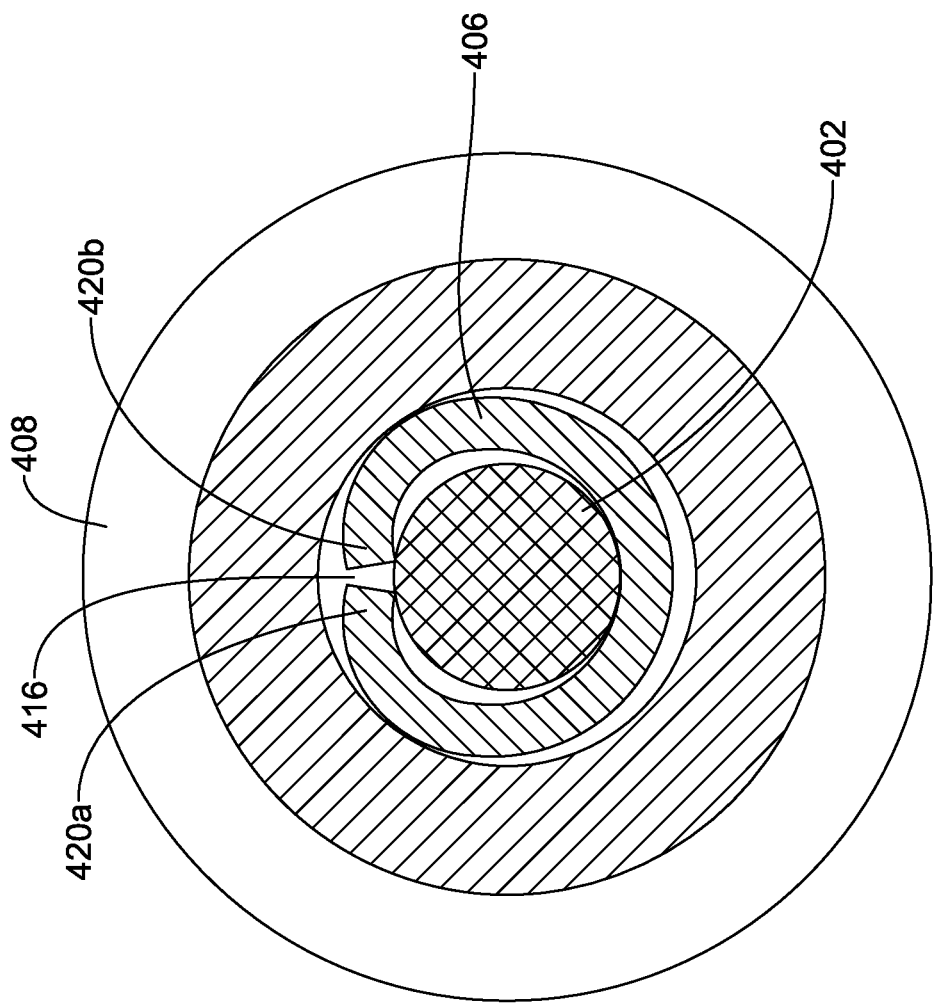
FIG. 17B is a partial cross-sectional view of the illustrative medical device system of FIG. 17A.

To lock the pusher wire 402 relative to the sheath 406, the locking element 408 is advanced further in the distal direction until the intermediate region 428 of the locking element 408 is disposed over the flaps 420 of the sheath 406. The flared distal portion 432 of locking element 408 may slide freely over the proximal end region 422 of the sheath. When the intermediate region 428 having the reduced diameter 442 of the locking element 408 reaches the outer sheath 406, the flaps 420 of the sheath 406 may fold over and be depressed onto an outer surface of the pusher wire 402. This is more clearly illustrated in FIG. 17B, which is a partial cross-section view of the illustrative medical device system 400, taken at line 17B-17B of FIG. 17A. For example, the locking element 408 may freely slide over the outer sheath 406 until the inner diameter of the locking element 408 is approximately equal to or less than an outer diameter of the sheath 406. Once the inner diameter of the locking element 408 begins to frictionally engage the outer surface of the sheath 406 more force may be required to continue distal movement of the locking element 408. As the locking element 408 is distally advanced further onto the sheath 406, the intermediate region 428 acts to deflect the flaps 420 of the sheath 406 inward and onto the wire 402. In some cases, the tapered lumen of the flared distal portion 434 may gradually deflect the flaps 420 inward. When advanced far enough, the locking element 408 wedges in place, creating the desired locking effect between the sheath 406 and the pusher wire 402. For example, the reduced diameter portion (e.g., having the second smaller inner diameter 442) of the lumen 438 of the locking element 408 may act as a wedge to pinch or exert a radially inward biasing force on an outer surface of the flaps 420 of the sheath 406 such that the outer diameter of the flaps 420 is decreased and the inner diameter of the arms is biased radially inward, as shown in FIG. 17B. As the inner diameter of the flaps 420 is reduced, the inner surface of the flaps 420 contacts and frictionally engages an outer surface of the pusher wire 402.

In the locked configuration illustrated in FIGS. 16, 17A, and 17B, the frictional engagement between the inner surface of the sheath 406 and the outer surface of the pusher wire 402 may preclude or inhibit axial (e.g., proximal and distal) and/or rotational movement of the pusher wire 402 within the lumen 410 of the sheath 406. In some embodiments, the flaps 420 are configured to promote inward deflection thereof. For example, the cut pattern of the slot 416 and/or slit 418 may be applied to promote collapse of the flaps 420 and to create a localized friction point between an inner surface of the sheath 406 (e.g., the inner surface of the flaps 420) and the pusher wire 402.

It is contemplated that the gradual decrease in the inner diameter of the locking element 408 may facilitate positioning of the locking element 408 over the sheath 406. For example, the inner diameter 440 of the locking element 408 at the distal portion 434 (and/or portions of the proximal portion 432 may be large enough to freely pass over the outer diameter of the sheath 406. As the inner diameter of the locking element 408 tapers (e.g., in the proximal direction towards the proximal end 424) to a dimension smaller than the outer diameter of the sheath 406, and is distally advanced far enough over the sheath 406, it promotes collapse of the flaps 420. This creates a friction lock between the sheath 406 and pusher wire 402 when the pusher wire 402 is positioned through the sheath 406.

When the user is ready to advance the implant, the locking element 408 may be removed proximally from the proximal region 422 of the sheath 406. This may allow the inner diameter of the sheath 406 adjacent to the flaps 420 to expand to the original configuration thus removing the friction lock and allowing the pusher wire 402 to move freely. Thus, as the sheath 406 is removed from the pusher wire 402, the sheath 406 does not engage or hang up on any portion of the pusher wire 402.

It is contemplated that when the locking element 408 is provided with a longitudinally extending slot, such as the slot 310 illustrated in the locking element 300, the locking element 408 may be free to drop off of the pusher wire 402 (e.g., via the slot) without having to be proximally retracted over an entirety of the length of the pusher wire 402 proximal to the sheath 406. Similarly, during loading of the locking element 408 at the time of manufacture, the locking element 408 can be placed over the pusher wire 402 rather than threading the locking element 408 over the pusher wire 402. As described above with respect to FIGS. 6 and 7, if so provided, a longitudinal slot may be sized such that the pusher wire 402 can fit through the slot, but not the sheath 406. This may ensure the locking element 408 does not fall off the sheath 406 in the locked position (e.g., FIGS. 16, 17A, and 17B) but can be easily removed from the pusher wire 402 once the locking element is in the unlocked configuration.

It is further contemplated that that locking element 408 may be formed from a material that is more rigid than or stiffer than the outer sheath 406. For example, the material for the locking element 408 may be selected such that the locking element 408 does not deflect when the tapered portion of the lumen 438 of the locking element 408 is advanced over the sheath 406 but rather forces the sheath 406 to deflect inward. In some embodiments, the locking element 408 may be formed from a bright (or other) color easily noticeable by the user.

Figure 18:
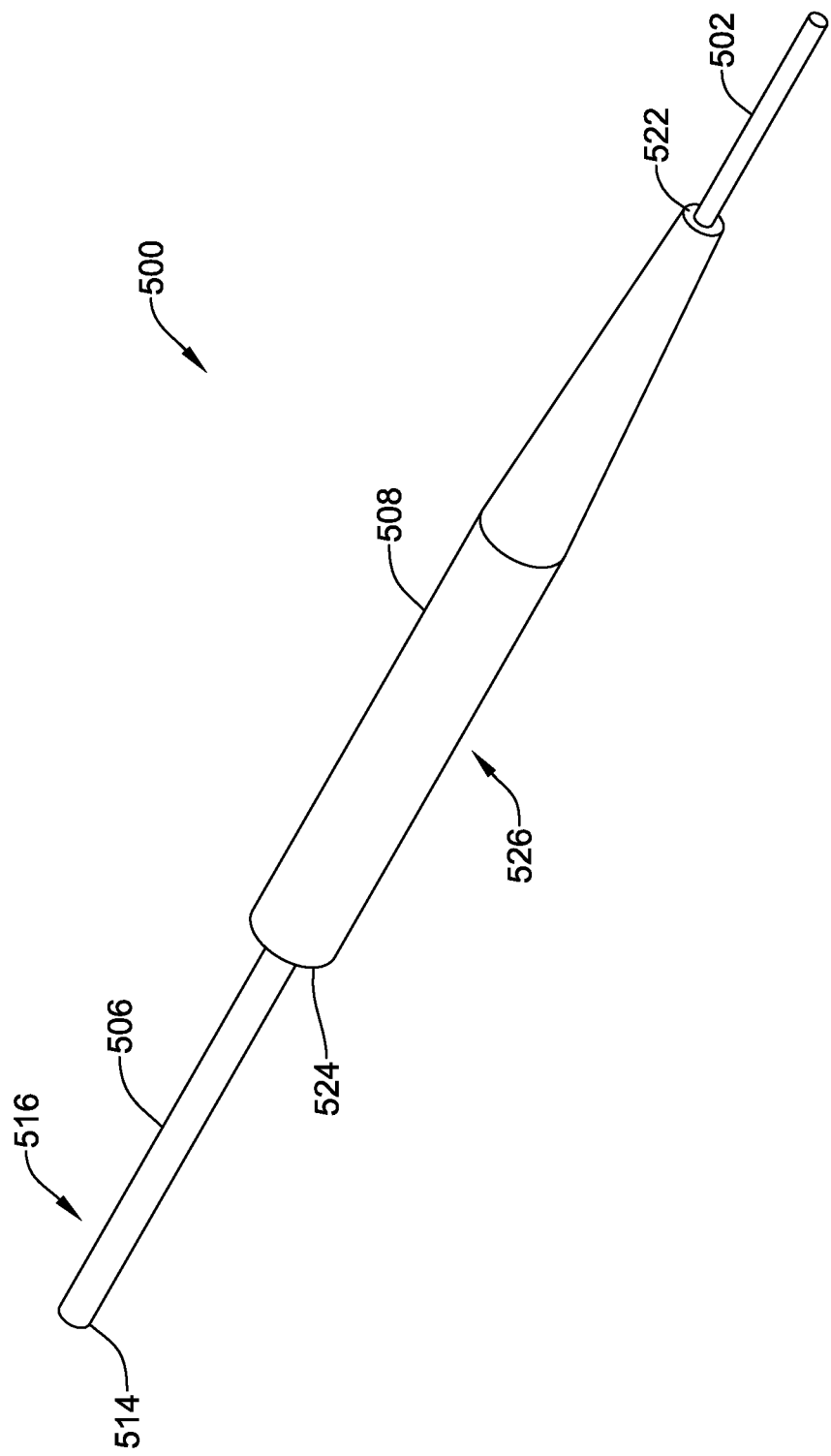
FIG. 18 is a perspective view of another example medical device system in a first configuration.
Figure 19:
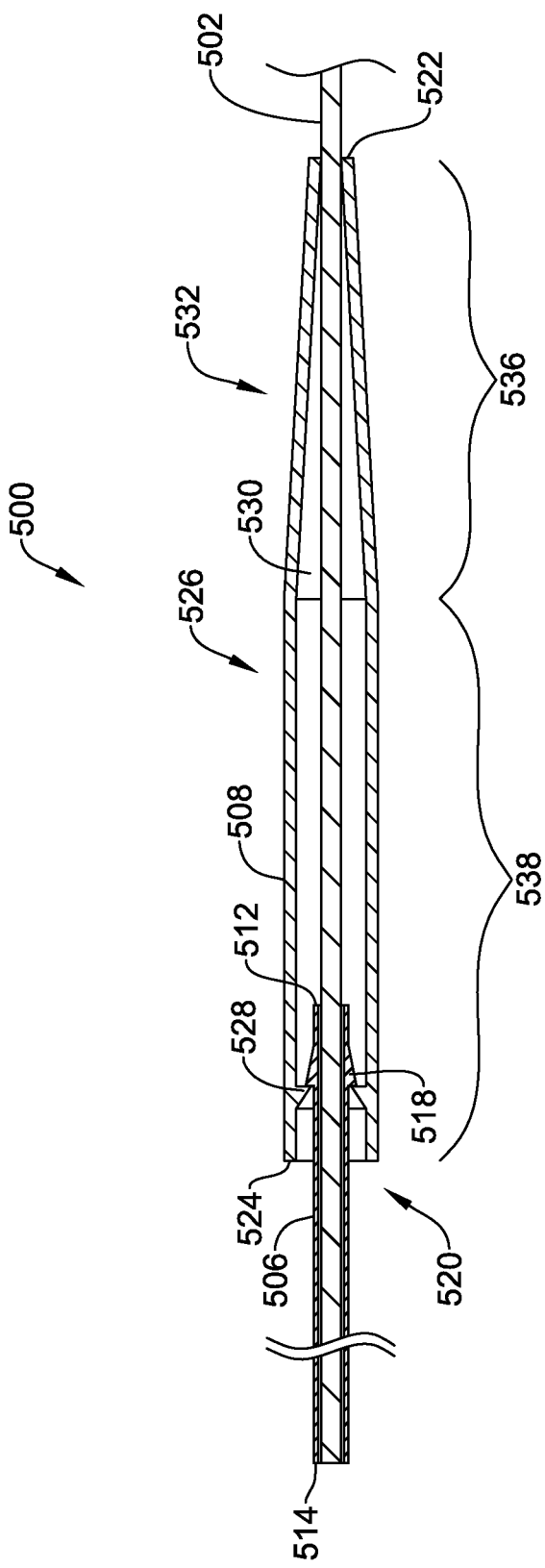
FIG. 19 is a partial cross-sectional view of the illustrative medical device system of FIG. 18.

FIG. 18 is a perspective view of an example medical device system 500 in an unlocked assembled configuration. FIG. 19 is a partial cross-sectional view of the medical device system 500 taken at line 19-19 of FIG. 18. The medical device system 500 may include a pusher wire 502, an implant (not explicitly shown), such as, but not limited to, an embolic coil, an introducer sheath 506, and a locking element 508. For simplicity, the implant is described as an embolic coil, but other suitable medical devices transported, delivered, used, released, etc. in a similar manner are also contemplated, including but not limited to, vascular occlusion devices coils, stents, embolic filters, replacement heart valves, other occlusion devices, and/or other medical implants, etc.

Embolic coils may be typically introduced into a blood vessel by using a microcatheter (not explicitly shown) that extends from a proximal point outside the patient's body to a distal point near the embolization site. An introducer sheath 506 containing the coil can be used to carry and protect the coil prior to insertion into the patient. Further, the introducer sheath 506 may be used to transfer the coil to the microcatheter and/or to assist in deploying the coil at a selected embolization site. The sheath 506 may be configured to protect the implant and maintain the implant in a deliverable orientation, until the implant is deployed. As will be described in more detail herein, the locking element 508 may be configured to limit movement (e.g., axial and rotational) of the pusher wire 502 and implant within the sheath 506 until the user is ready to advance the implant out of the sheath 506.

The sheath 506 may be a tubular member including a proximal end 512 (e.g., FIG. 19), a distal end 514, and an intermediate region 516 positioned therebetween. Some suitable but non-limiting materials for the sheath 506, for example, polymer materials, composite materials, etc., are described below. The sheath 506 may define a lumen 510 extending from the proximal end 512 to the distal end 514. The pusher wire 502 and implant may be slidably disposed within the lumen 510 of the sheath 506 such that the pusher wire 502 and the implant are radially inwards of the sheath 506. The implant may be disposed proximate the distal end 514 of the sheath 506. The pusher wire 502 may be axially slidable between an interlocked position and a released position. The pusher wire 502 may be configured to be releasably attached to the implant. The implant may be configured to expand from a delivery configuration to a deployed configuration. The pusher wire 502 may generally be a solid wire or shaft, but may also be tubular in some embodiments. Some suitable but non-limiting materials for the pusher wire 502, for example metallic materials, polymer materials, composite materials, etc., are described below. As will be described in more detail herein, the pusher wire 502 may be releasably secured to the sheath 506 via the locking element 508 to limit axial and/or rotationally movement of the pusher wire 502 within the sheath 506.

It is contemplated that a proximal end region 520 of the sheath 506 may be formed from polypropylene or a material similar thereto. The durometer of the proximal end region 520 may be manipulated to produce a desired locking effect. In some cases, other portions of the sheath 506 may be formed from a same material as the proximal end region 520 while in other cases, other portions of the sheath 506 may be formed from a different material as the proximal end region 520. For example, the sheath 506 may include a polyimide distal tip (although this is not required).

Referring additionally to FIG. 19, the sheath 506 may include an angled protrusion 518 adjacent the proximal end 512 and extending radially outward from an outer surface of the sheath 506. The angled protrusion 518 may cooperate with a corresponding protrusion 528 on the locking element 508 to allow the locking element 508 to be distally advanced over the sheath 506 while providing a mechanical stop that limits actuation of the locking element 508 in the proximal direction. In some instances, the angled protrusion 518 may be a single component extending about an entire circumference (e.g., 360°) of the sheath 506. In other cases, the angled protrusion 518 may be formed from a plurality of individual protrusions which are spaced (uniformly or eccentrically) about the circumference of the sheath 506. The angled protrusion 518 may have an outer diameter which decreases in the proximal direction (e.g., towards the proximal end 512). The distal end of the angled protrusion 518 may be generally planar and have an outer diameter that is greater than an inner diameter of the proximal end of the protrusion 528 of the locking element 508, as will be described in more detail herein. The distal end of the angled protrusion 518 may extend generally orthogonal to a longitudinal axis of the sheath 506 while the angled surface extends at an angle that is non-orthogonal and non-parallel to the longitudinal axis of the sheath 506.

The locking element 508 may be a tubular member having a proximal end 522, a distal end 524, and an intermediate region 526 positioned therebetween. The locking element 508 may have a tapered or sloped outer diameter over a proximal region 536 that increases from the proximal end 522 towards and into the intermediate region 526. The locking element 508 may include a distal region 538 having a generally uniform or constant outer diameter. The locking element 508 may define a lumen 530 extending from the proximal end 522 to the distal end 524. As will be discussed in more detail herein, a portion of the lumen 530 of the locking element 508 may be sized to slide freely over the sheath 506 while another portion of the lumen 530 may be sized to exert a radially inward compressing force on the sheath 506, as will be described in more detail herein. Thus, in some configurations, at least a portion of the sheath 506 may be radially inward of the locking element 508.

The locking element 508 may be formed in a variety of different manners. For example, the locking element 508 may be injection molded, heat shrunk, 3-D printed, etc. The locking element 508 may be formed from a variety of different materials such as, but not limited to, hard or soft polymers, metals, composites, etc.

The locking element 508 may have a variable inner diameter. For example, in some embodiments, the locking element 508 may have an inner diameter which increases in a sloped manner over the proximal region 536 in the distal direction from a first, smaller, inner diameter adjacent the proximal end 522 to a second, larger, inner diameter. The second inner diameter 138 may be approximately constant or uniform over a distal region 538 of the locking element 508. In some cases, while not explicitly shown, the transition from the first inner diameter to the second inner diameter 138 may be an abrupt or step-wise transition. The proximal region 536 and/or the distal region 538 may vary, as desired. Further, the slope of the proximal region 536 may vary, as desired. The dimensions (e.g., inner diameter, outer diameter, length, slope, etc.) of the tapered proximal region 536 and/or the distal region 538 may be changed to create the desired locking effect (described in more detail herein).

In some embodiments, a wall thickness of the locking element 508 may remain generally uniform over the proximal and/or distal regions 536, 538 of the locking element 508. In such an instance, the inner diameter and the outer diameter of the locking element 508 may vary (e.g., may be sloped in a similar manner) along the proximal region 536. For example, the outer diameter of the locking element 508 may increase from a first outer diameter at the proximal end 522 to a second outer diameter (greater than the first outer diameter) over the proximal region 536, as the inner diameter increases. In some embodiments, the wall thickness may vary over the proximal and/or distal regions 536, 538 of the locking element 508. The second, larger, inner diameter may be sized such that the locking element 508 can slide freely over the sheath 506. The first, smaller, inner diameter may be sized to apply a compressive, or radially inward force on the outer surface of the sheath 506, as will be described in more detail herein.

The locking element 508 may include an angled protrusion 528 adjacent the distal end 524 and extending radially inward from an inner surface of the locking element 508. The angled protrusion 528 may cooperate with the protrusion 518 on the sheath 506 to allow the locking element 508 to be distally advanced over the sheath 506 while providing a mechanical stop that limits actuation of the locking element 508 in the proximal direction. In some instances, the angled protrusion 528 may be a single component extending about an entire inner surface of the lumen 530 (e.g., 360°) of the locking element 508. In other cases, the angled protrusion 528 may be formed from a plurality of individual protrusions which are spaced (uniformly or eccentrically) about the inner surface of the lumen 530. The angled protrusion 528 may have an inner diameter which decreases in the distal direction (e.g., towards the distal end 524). The proximal end of the angled protrusion 528 may be generally planar and have an inner diameter that is less than an outer diameter of the distal end of the protrusion 518 of the sheath 506. The proximal end of the angled protrusion 528 may extend generally orthogonal to a longitudinal axis of the locking element 508 while the angled surface extends at an angle that is non-orthogonal and non-parallel to the longitudinal axis of the locking element 508.

The sloped surfaces of the angled protrusions 518, 528 may be structured such that the angled protrusion 518 on the sheath 506 essentially functions as a ramp for the angled protrusion 528 on the locking element 508. This may allow the locking element 508 to be loaded onto the proximal end region 520 of the sheath 506 by advancing the distal end 512 of the sheath 506 through the distal end 524 of the locking element. Once loaded onto the sheath 506, proximal retraction of the locking element 508 will be limited. For example, the generally planar proximal end of the angled protrusion 528 on the locking element 508 will abut the generally planar distal end of the angled protrusion 518 on the sheath 506 creating a mechanical stop thus limiting the axial movement of the locking element 508. This may allow the locking element 508 to be moved between the locked (see, for example, FIG. 20) and unlocked configuration over a shorter distance and without fully removing it from the pusher wire 502.

It is contemplated that the configuration of the locking element 508 may be adjusted to create the desired effect. For example, one or more of the inner diameters may be made larger or smaller to accommodate different sizes of sheaths 506. Further, the proximal and/or distal regions 536, 538 may be longer, shorter, less angled, more angled, etc. In another example, the outer diameter of the locking element 508 may be increased or decreased to facilitate handling. It is further contemplated that the outer surface of the locking element 508 may include features to improve ergonomic handling, such as, but not limited to, bumps, waves, texturing, or indentations to improve gripability. In some cases, the sheath 506 and/or the locking element 508 may include visual indicia to guide the user in manipulation of the locking element 508. In some cases, the overall length of the locking element 508 can be increased or decreased, as desired. It is further contemplated that the locking element 508 may be large enough to make it easy to handle but not so large as to be incompatible with other components, such as, but not limited to packaging.

While the medical device system 500 is described with respect to a particular locking element 508, it should be understood that any of the locking elements described herein may be substituted for the locking element 508. To position the locking element 508 such that it can be used to secure the pusher wire 502, the locking element 508 is distally advanced over the proximal end region 520 of the sheath 506 from the proximal end 512. It should be understood that the varying lengths of the locking element 508 may be positioned over the sheath 506 in an unlocked configuration. However, an entirety of the locking element 508 may not be disposed over sheath 506 in the unlocked configuration. For example, the proximal region 536 of the locking element 508 having the reduced inner diameter may be only partially disposed over the sheath 506 or not over the sheath 506 at all. In this configuration, the pusher wire 502 is free to slide axially (e.g., proximally and distally) and/or rotate within the lumen 510 of the sheath 506. As described above, the inner diameter of the sheath 506 may remain constant, or substantially constant from the proximal end 512 to the distal end 514.

Figure 20:
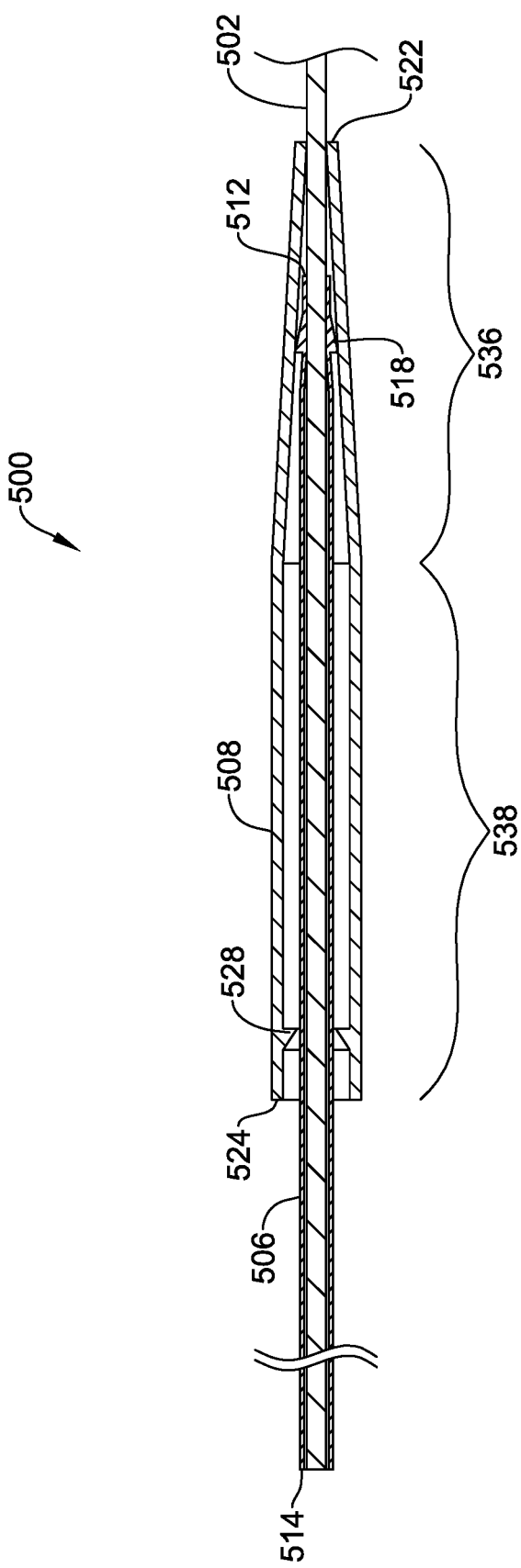
FIG. 20 is a partial cross-sectional view of the illustrative medical device system of FIG. 18 in a second configuration.

To lock the pusher wire 502 relative to the sheath 506, the locking element 508 is advanced further in the distal direction until the proximal region 536 of the locking element 508 is disposed over the proximal end region 520 of the sheath 506. FIG. 20 is a partial cross-sectional view of the medical device system 500 in a locked configuration. As described above, the distal portion 538 and a portion of the proximal portion 536 of locking element 508 may slide freely over the proximal end region 520 of the sheath. When proximal portion 536 having the reduced diameter of the locking element 508 reaches the outer sheath 506, the sheath 506 may be depressed onto an outer surface of the pusher wire 502. For example, the locking element 508 may freely slide over the outer sheath 506 until the inner diameter of the locking element 508 is approximately equal to or less than an outer diameter of the sheath 506. Once the inner diameter of the locking element 508 begins to frictionally engage the outer surface of the sheath 506 more force may be required to continue distal movement of the locking element 508. As the locking element 508 is distally advanced further onto the sheath 506, the tapered region (e.g., the proximal region 536) acts to deflect the sheath 506 inward and onto the wire 502. When advanced far enough, the locking element 508 wedges in place, creating the desired locking effect between the sheath 506 and the pusher wire 502. For example, the tapered portion of the lumen 530 of the locking element 508 may act as a wedge to pinch or exert a radially inward biasing force on an outer surface of the sheath 506 such that the outer diameter of sheath 506 is decreased and the inner diameter of the sheath 506 is biased radially inward, as shown in FIG. 20. As the inner diameter of the sheath 506 is reduced, the inner surface of the sheath 506 contacts and frictionally engages an outer surface of the pusher wire 502.

In the locked configuration illustrated in FIG. 20, the frictional engagement between the inner surface of the sheath 506 and the outer surface of the pusher wire 502 may preclude or inhibit axial (e.g., proximally and distally) and/or rotational movement of the pusher wire 502 within the lumen 510 of the sheath 506. In some embodiments, the sheath 506 may configured to promote inward deflection thereof. For example, the sheath 506 may include cuts, slots, have a reduced thickness, be more flexible, etc. to promote collapse of the sheath 506 and to create a localized friction point between an inner surface of the sheath 506 and the pusher wire 502.

It is contemplated that the gradual decrease in the inner diameter of the locking element 508 may facilitate positioning of the locking element 508 over the sheath 506. For example, the inner diameter of the locking element 508 at the distal portion 538 (and/or portions of the proximal portion 536 may be large enough to freely pass over the outer diameter of the sheath 506. As the inner diameter of the locking element tapers (e.g., in the proximal direction towards the proximal end 522) to a dimension smaller than the outer diameter of the sheath 506, and is distally advanced far enough over the sheath 506, it promotes collapse of the sheath 506. This creates a friction lock between the sheath 506 and pusher wire 502 when the pusher wire 502 is positioned through the sheath 506.

When the user is ready to advance the implant, the locking element 508 may be proximally displaced (but not entirely removed) from the proximal region 520 of the sheath 506. This may allow the inner diameter of the sheath 506 to expand to the original configuration thus removing the friction lock and allowing the pusher wire 502 to move freely. Thus, as the sheath 506 is removed from the pusher wire 502, the sheath 506 does not engage or hang up on any portion of the pusher wire 502.

It is contemplated that that locking element 508 may be formed from a material that is more rigid than or stiffer than the outer sheath 506. For example, the material for the locking element 508 may be selected such that the locking element 508 does not deflect when the tapered portion of the lumen 530 of the locking element 508 is advanced over the sheath 506 but rather forces the sheath 506 to deflect inward. In some embodiments, the locking element 508 may be formed from a bright (or other) color easily noticeable by the user.

Figure 21:
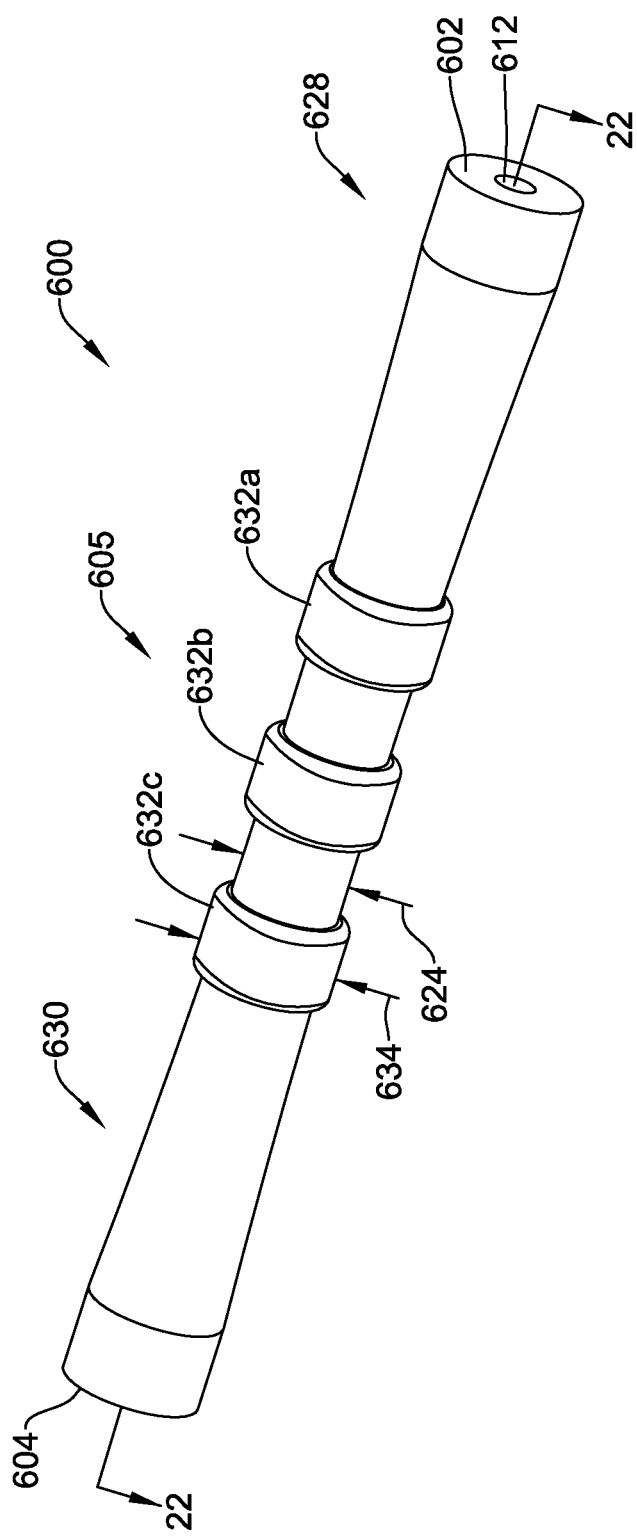
FIG. 21 is a perspective view of another illustrative locking mechanism.

FIG. 21 illustrates a perspective view of another illustrative locking element 600. The locking element 600 may be similar in form and function to the illustrative locking mechanism 108 described herein and may be used with a medical device system, such as the medical device system 100 described herein. The locking element 600 may be a tubular member having a proximal end 602, a distal end 604, and an intermediate region 605 positioned therebetween. The locking element 600 may define a lumen 612 extending from the proximal end 602 to the distal end 604. A portion of the lumen 612 of the locking element 600 may be sized to slide freely over a sheath, such as the sheath 106 described herein, while another portion of the lumen 612 may be sized to exert a radially inward or compressive force on the sheath 106, as will be described in more detail herein. Thus, in some configurations, at least a portion of the sheath 106 may be radially inward of the locking element 600.

The locking element 600 may have a tapered or sloped outer diameter over a proximal region 628 extending from the proximal end 602 towards and into the intermediate region 605. Similarly, the locking element 600 may have a tapered or sloped outer diameter over a distal region 630 extending from the distal end 604 towards and into the intermediate region 605. However, in some cases, one or both the proximal region 628 and the distal region 630 may have a generally constant outer diameter or the diameter may increase towards the intermediate region 605 as desired. The intermediate region 605 may include plurality of raised regions or circumferential ribs 632a, 632b, 632c (collectively, 632). The circumferential ribs 632 may have an outer diameter 634 that is greater than an outer diameter 624 of the intermediate region 605 between the ribs 632. The circumferential ribs 632 may extend about an entire perimeter of the locking element 600 or less than an entire perimeter, as desired. It is contemplated that the circumferential ribs 632 may increase the tactility of the locking element 600 and/or make the locking element 600 easier to grip or handle. The number of circumferential ribs 632 (e.g., fewer than three or greater than three), the size of the circumferential ribs 632 (e.g., increasing or decreasing the diameter 634), the geometry of the circumferential ribs 632 (extending about less than an entire perimeter, having a different shape, etc.), and/or the spacing of the circumferential ribs 632 can be varied to enhance or diminish the tactility or gripability of the locking element 600, as desired.

The locking element 600 may be formed in a variety of different manners. For example, the locking element 600 may be injection molded, heat shrunk, 3-D printed, etc. The locking element 600 may be formed from a variety of different materials such as, but not limited to, hard or soft polymers, metals, composites, etc.

Figure 22:
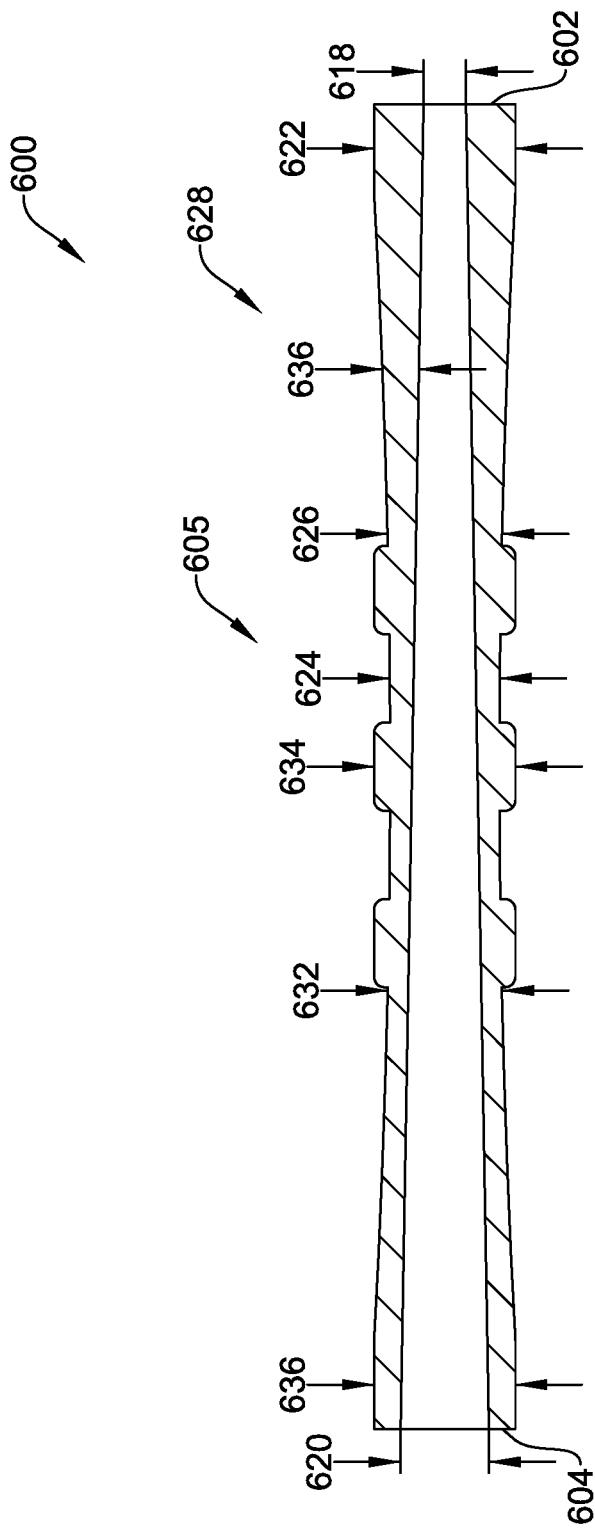
FIG. 22 is a cross-sectional view of the illustrative locking mechanism of FIG. 21.

FIG. 22 is a cross-sectional view of the locking element 600 taken at line 22-22 of FIG. 21. The locking element 600 may have a variable outer diameter and a variable inner diameter. For example, in some embodiments, the locking element 600 may have an inner diameter which increases in a sloped manner in the distal direction from a first inner diameter 618 adjacent the proximal end 602 to a second inner diameter 620 adjacent the distal end 604. Further, the slope of the inner surface may vary, as desired. The second, larger inner diameter 620 may be sized such that the distal region 630 of the locking element 600 can slide freely over the sheath 106. The first, smaller inner diameter 618 may be sized such that the proximal region 628 is configured to apply a compressive, or radially inward force on the outer surface of the sheath 106.

In some embodiments, a wall thickness 636 of the locking element 600 may vary over a length of the locking element 600. In some cases, the wall thickness 636 is not directly correlated to the inner diameter of the locking element 600. In other cases, the wall thickness 636 may reduce in size as the inner diameter increases. These are just some examples. The outer diameter of the locking element 600 may decrease from a first outer diameter 624 at the proximal end 602 to a second outer diameter 626 (less than the first outer diameter 624) adjacent to the intermediate region 605. The outer diameter of the locking element 600 may decrease from a third outer diameter 636 at the proximal end 602 to a fourth outer diameter 632 (less than the third outer diameter 636) adjacent to the intermediate region 605. In some embodiments the first outer diameter 622 and the third outer diameter 636 may be approximately equal, although this is not required. Similarly, the second outer diameter 626 and the fourth outer diameter 632 may be approximately equal, although this is not required.

It is contemplated that the configuration of the locking element 600 may be adjusted to create the desired effect. The dimensions (e.g., inner diameter, outer diameter, length, slope, etc.) of the tapered inner diameter may be changed to create the desired locking effect. For example, one or more of the inner diameters 618, 620 may be made larger or smaller to accommodate different sizes of sheaths 106. In another example, the outer diameter of the locking element 600 may be increased or decreased to facilitate handling. It is further contemplated that the outer surface of the locking element 600 may include features to improve ergonomic handling, such as, but not limited to, bumps, waves, texturing, or indentations to improve gripability. In some cases, the sheath 106 and/or the locking element 600 may include visual indicia to guide the user in manipulation of the locking element 600. In some cases, the overall length of the locking element 600 can be increased or decreased, as desired. It is further contemplated that the locking element 600 may be large enough to make it easy to handle but not so large as to be incompatible with other components, such as, but not limited to packaging.

Figure 23:
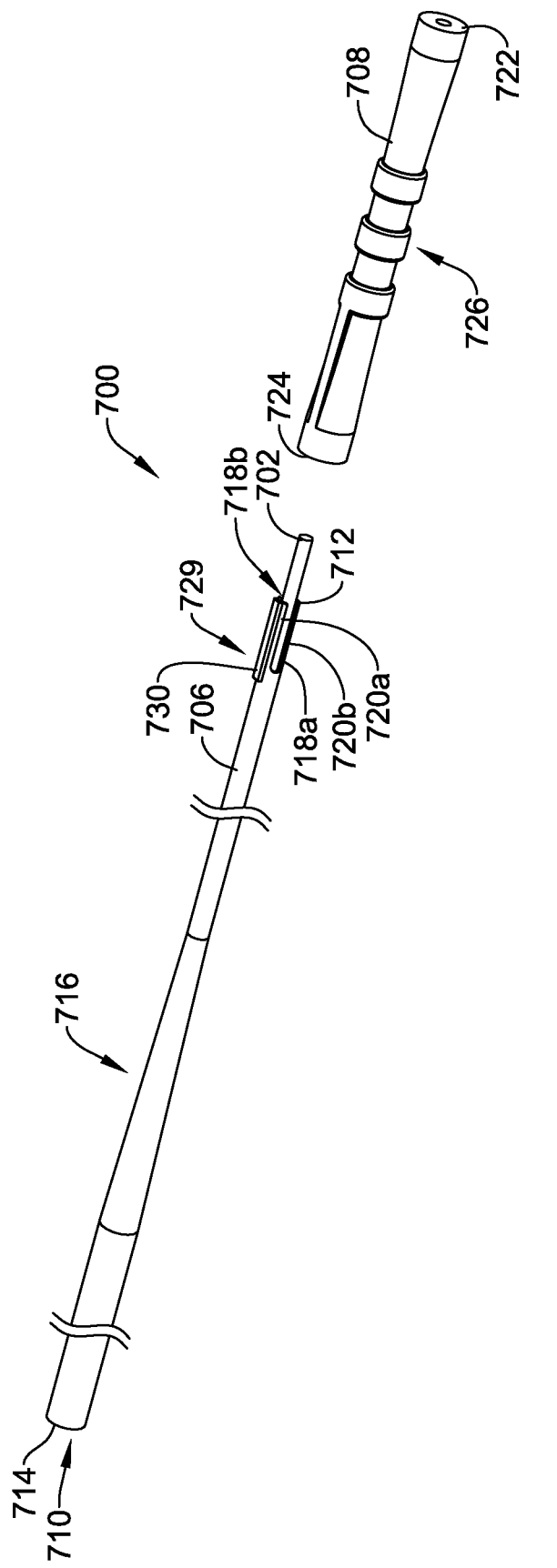
FIG. 23 is a perspective view of another example medical device system in a first configuration.

FIG. 23 is a perspective view of another illustrative medical device system 700 in a partially unassembled configuration. The medical device system 700 may include a pusher wire 702, an implant (not explicitly shown), such as, but not limited to, an embolic coil, an introducer sheath 706, and a locking element 708. For simplicity, the implant is described as an embolic coil, but other suitable medical devices transported, delivered, used, released, etc. in a similar manner are also contemplated, including but not limited to, vascular occlusion devices coils, stents, embolic filters, replacement heart valves, other occlusion devices, and/or other medical implants, etc. While the medical device system 400 is described with respect to a particular locking element 708, it should be understood that any of the locking elements described herein, including but not limited to the locking elements 108, 200, 300, 408, 508, 600, 800, may be substituted for the locking element 408.

Embolic coils may be typically introduced into a blood vessel by using a microcatheter (not explicitly shown) that extends from a proximal point outside the patient's body to a distal point near the embolization site. An introducer sheath 706 containing the coil can be used to carry and protect the coil prior to insertion into the patient. Further, the introducer sheath 706 may be used to transfer the coil to the microcatheter and/or to assist in deploying the coil at a selected embolization site. The sheath 706 may be configured to protect the implant and maintain the implant in a deliverable orientation, until the implant is deployed. As will be described in more detail herein, the locking element 708 may be configured to limit movement (e.g., axial and rotational) of the pusher wire 702 and implant within the sheath 706 until the user is ready to advance the implant out of the sheath 706.

The sheath 706 may be a tubular member including a proximal end 712, a distal end 714, and an intermediate region 716 positioned therebetween. Some suitable but non-limiting materials for the sheath 706, for example, polymer materials, composite materials, etc., are described below. The sheath 706 may define a lumen 710 extending from the proximal end 712 to the distal end 714. The pusher wire 702 and implant may be slidably disposed within the lumen 710 of the sheath 706 such that the pusher wire 702 and the implant are radially inwards of the sheath 706. The implant may be disposed proximate the distal end 714 of the sheath 706. The pusher wire 702 may be axially slidable between an interlocked position and a released position. The pusher wire 702 may be configured to be releasably attached to the implant. The implant may be configured to expand from a delivery configuration to a deployed configuration. The pusher wire 702 may generally be a solid wire or shaft, but may also be tubular in some embodiments. Some suitable but non-limiting materials for the pusher wire 702, for example metallic materials, polymer materials, composite materials, etc., are described below. As will be described in more detail herein, the pusher wire 702 may be releasably secured to the sheath 706 via the locking element 708 to limit axial and/or rotational movement of the pusher wire 702 within the sheath 706.

The sheath 706 may have a first slot 718a and a second slot 718b (collectively, 718) extending distally from the proximal end 712. The first and second slots 718a, 718b may be positioned across from another or spaced approximately 180° about the circumference of the sheath 706. While the sheath 706 is described as having two slots, the sheath 706 may include fewer than two or more than two slots, as desired. The slots 718 may extend less than an entire length of the sheath 706. The slots 718 may remove material from the sheath 706 to create flexible arms or members 720a, 720b (collectively, 720). While the sheath 706 is described as having two arms 720, it should be understood the number of flexible arms may vary with the number of slots 718 and there can be fewer than two or more than two flexible arms, as desired. Further, the slots 718 may be uniformly or eccentrically distributed about a circumference of the sheath 706. The length and/or size of the slots 718 (and/or the arms 720) may vary to produce different degrees of wedging (between the locking element 708 and the pusher wire 702) and locking capabilities.

The sheath 706 may further include a raised projection 730 extending radially from an outer surface thereof. The raised projection 730 may be positioned adjacent to the proximal end region 729 of the sheath 706. In some cases, the raised projection 730 may extend distally from the proximal end 712 of the sheath 706. However, this is not required. The raised projection 730 may be a rectangular prism, such as, but not limited to a ridge or other three-dimensional structure configured to engage a mating groove, notch, or recess within the locking element 708, as will be described in more detail herein.

It is contemplated that a proximal end region 729 of the sheath 706 may be formed from polypropylene or a material similar thereto. The durometer of the proximal end region 729 may be manipulated to produce a desired locking effect. In some cases, other portions of the sheath 706 may be formed from a same material as the proximal end region 729 while in other cases, other portions of the sheath 706 may be formed from a different material as the proximal end region 729. For example, the sheath 706 may include a polyimide distal tip (although this is not required).

Figure 24:
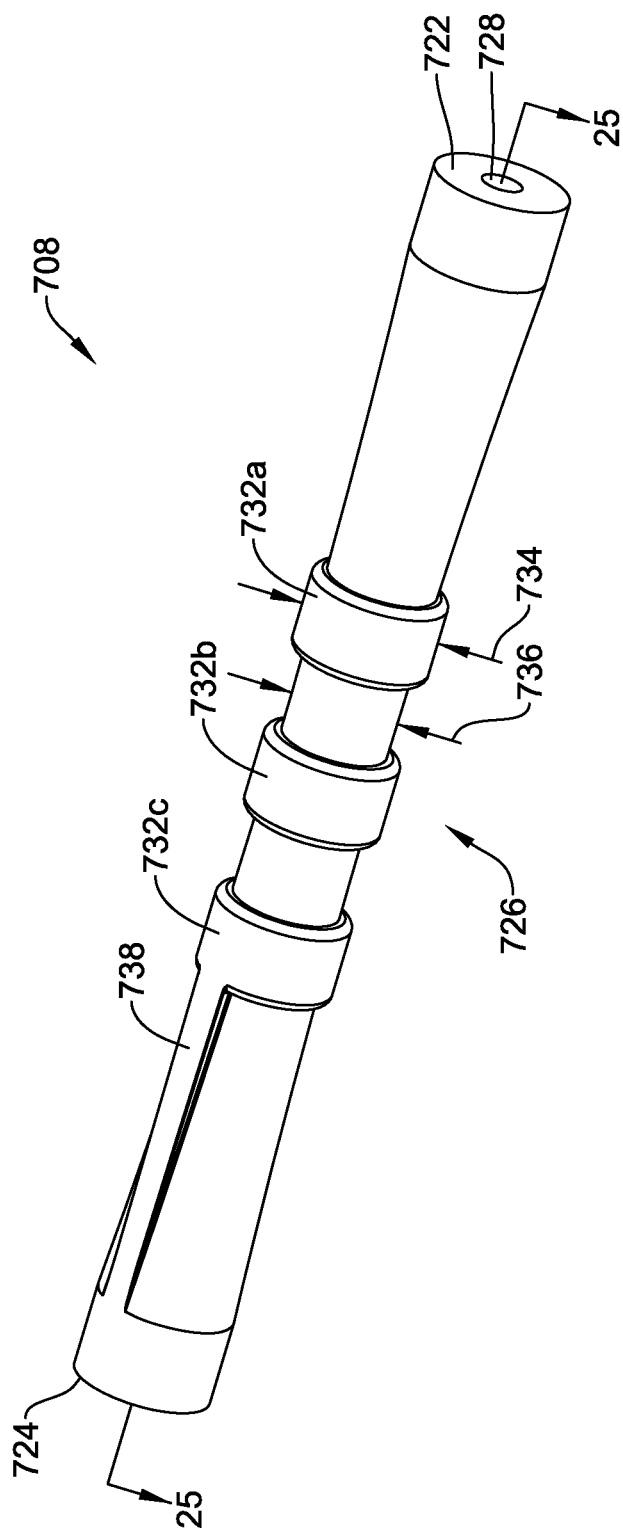
FIG. 24 is a perspective view of an illustrative locking mechanism.

Referring additionally to FIG. 24, which illustrates a perspective view of the locking element 708, the locking element 708 may be a tubular member having a proximal end 722, a distal end 724, and an intermediate region 726 positioned therebetween. The locking element 708 may have a generally hourglass shaped outer profile. For example, the outer diameter may generally decrease from the proximal end 722 towards the intermediate region 726 and increase from the intermediate region 726 to the distal end 724. However, this is not required. The outer profile of the locking element 708 may take any shape desired.

The locking element 708 may define a lumen 728 extending from the proximal end 722 to the distal end 724. As will be discussed in more detail herein, a portion of the lumen 728 of the locking element 708 may be sized to slide freely over the sheath 706 while another portion of the lumen 728 may be sized to exert a radially inward compressing force on the sheath 706, as will be described in more detail herein. Thus, in some configurations, at least a portion of the sheath 706 may be radially inward of the locking element 708.

The intermediate region 726 may include plurality of raised regions or circumferential ribs 732a, 732b, 732c (collectively, 732). The circumferential ribs 732 may have an outer diameter 734 that is greater than an outer diameter 736 of the intermediate region 726 between the ribs 732. The circumferential ribs 732 may extend about an entire perimeter of the locking element 708 or less than an entire perimeter, as desired. It is contemplated that the circumferential ribs 732 may increase the tactility of the locking element 708 and/or make the locking element 708 easier to grip or handle. The number of circumferential ribs 732 (e.g., fewer than three or greater than three), the size of the circumferential ribs 732 (e.g., increasing or decreasing the diameter 734), the geometry of the circumferential ribs 732 (extending about less than an entire perimeter, having a different shape, etc.), and/or the spacing of the circumferential ribs 732 can be varied to enhance or diminish the tactility or gripability of the locking element 708, as desired.

The locking element 708 may further include one or more features to provide a visual cue as to how the locking element 708 should be assembled with the sheath 706. For example, the feature may be configured to provide an indication to the user how to align the locking element 708 with the sheath 706 such that the locking element 708 may be slid over the sheath 706. In some cases, the feature may be incorporated into the structure of the locking element 708. For example, in the embodiment illustrated in FIG. 24, the locking element 708 includes an axially extending (e.g., parallel to a longitudinal axis of the locking element 708) raised portion 738. The raised portion 738 is radially aligned with an internal groove 740 (see, for example, FIGS. 25 and 26) formed in an inner surface of the locking element 708. As will be described in more detail herein, the groove 740 may be configured to align with the raised projection 730 of the sheath 706 to allow for selective assembly of the locking element 708 with the sheath 706. The raised portion 738 is just one example of a feature that may be used to provide visual cues to the operator. Other features may include visual markings on an outer surface of the locking element 708 (e.g., arrows, words, etc.) or other structural features, as desired.

The locking element 708 may be formed in a variety of different manners. For example, the locking element 708 may be injection molded, heat shrunk, 3-D printed, etc. The locking element 708 may be formed from a variety of different materials such as, but not limited to, hard or soft polymers, metals, composites, etc. It is further contemplated that that locking element 708 may be formed from a material that is more rigid than or stiffer than the outer sheath 706. For example, the material for the locking element 708 may be selected such that the locking element 708 does not deflect when the tapered portion of the lumen 728 of the locking element 708 is advanced over the sheath 706 but rather forces the sheath 706 to deflect inward. In some embodiments, the locking element 708 may be formed from a bright (or other) color easily noticeable by the user.

Figure 25:
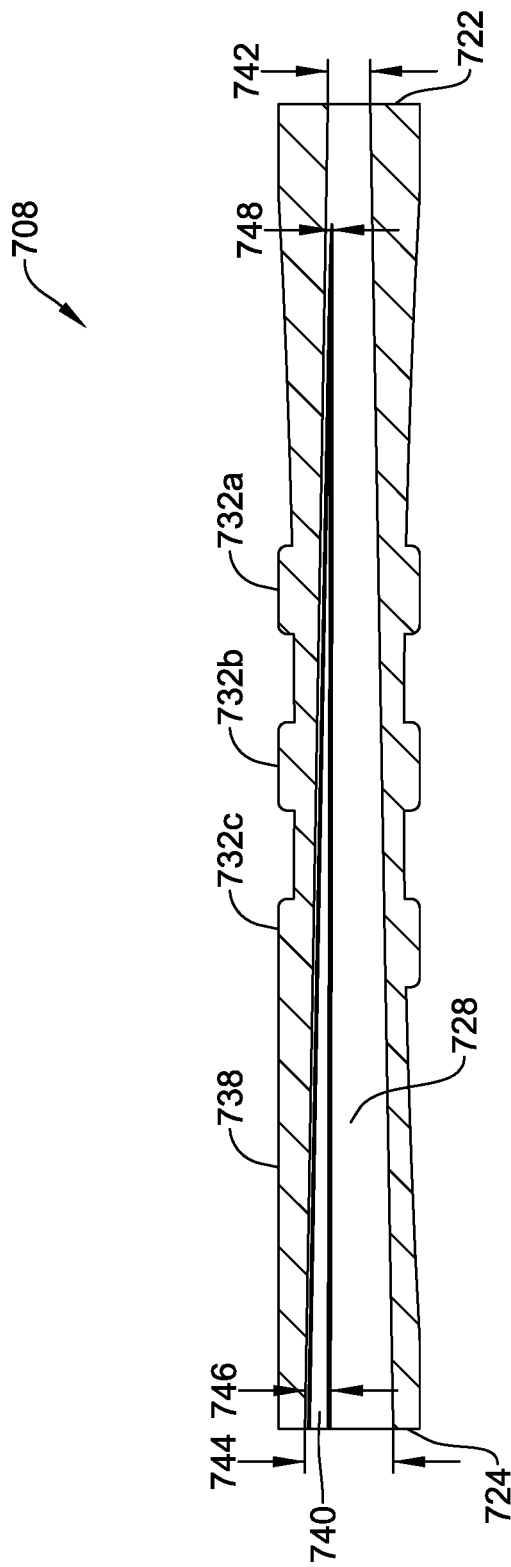
FIG. 25 is a cross-sectional view of the illustrative locking mechanism of FIG. 24.
Figure 26:
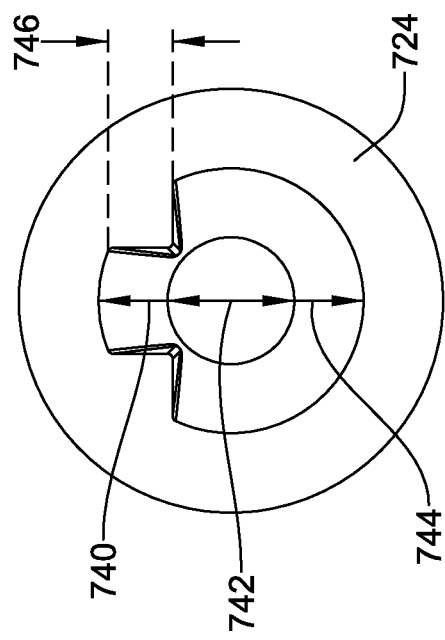
FIG. 26 is a distal end view of the illustrative locking mechanism of FIG. 24.

FIG. 25 is a cross-sectional view of the locking element 708 taken at line 25-25 of FIG. 24. FIG. 26 is a distal end view of the locking element 708. The locking element 708 may have a variable inner cross-sectional dimension. In some cases, the lumen 728 may have a generally tapered configuration. For example, in some embodiments, the lumen 728 of the locking element 708 may have a first cross-sectional dimension 742 adjacent to the proximal end 722 thereof which increases in the distal direction to a second cross-sectional dimension 744 adjacent a distal end 724 thereof which is greater than the first cross-sectional dimension 742. The cross-sectional dimension may gradually transition in a tapered or sloped manner. In other embodiments, the cross-sectional dimension may vary in an abrupt or step-wise manner. These are just some examples. In some cases, a wall thickness of the locking element 708 may vary over at least a portion of the locking element.

However, this is not required. The dimensions (e.g., inner diameter, outer diameter, length, slope, etc.) of the locking element 708 may be changed to create the desired locking effect (described in more detail herein). The distal inner cross-sectional dimension 744 may be sized such that the locking element 708 can slide freely over the sheath 706. The proximal, smaller inner cross-sectional dimension 742 may be sized to apply a compressive, or radially inward force on the outer surface of the sheath 706.

It is contemplated that the configuration of the locking element 708 may be adjusted to create the desired effect. For example, one or more of the inner cross-sectional dimensions 742, 744 may be made larger or smaller to accommodate different sizes of sheaths 706. In another example, the outer diameter of the locking element 708 may be increased or decreased to facilitate handling. It is further contemplated that the outer surface of the locking element 708 may include features to improve ergonomic handling, such as, but not limited to, bumps, waves, texturing, or indentations to improve gripability. In some cases, the sheath 706 and/or the locking element 708 may include visual indicia to guide the user in manipulation of the locking element 708. In some cases, the overall length of the locking element 708 can be increased or decreased, as desired. It is further contemplated that the locking element 708 may be large enough to make it easy to handle but not so large as to be incompatible with other components, such as, but not limited to packaging.

As described above, the locking element 708 may further include an axially extending (e.g., parallel to a longitudinal axis of the locking element) notch or groove 740. As shown in FIG. 25, the groove 740 may have a first depth 746 adjacent to the distal end 724 and a second depth 748 adjacent to the proximal end 722. The second depth 748 is less than the first depth 746 such that a distal portion of the locking element 708 can freely slide over the sheath 706 when the groove 740 is aligned with the raised projection 730 of the sheath 706. As the locking element 708 is distally advanced, the lumen 728 exerts a radially inward or compressive force on the sheath 706.

Together, the radial projection 730 of the sheath 706 and the groove 740 of the locking element 708 may create an orientation dependent assembly. For example, the locking element 708 is oriented such that the groove 740 is aligned with the radial projection 730 of the sheath 706 to allow the locking element 708 to distally advance over the sheath 706. Misalignment of the groove 740 and radial projection 730 may lead to an interference between the locking element 708 and the sheath 706 that would prevent passage of the sheath 706 into the locking element 708 and subsequent locking of the pusher wire 702. This may prevent undesired re-engagement of the locking element 708 and sheath 706 during use of the system 700 in the event the locking element 708 is not fully removed from the pusher wire 702. In the absence of orientation dependent features, if the locking element 708 is left hanging on the pusher wire 702, it may unintendedly re-engage with the sheath 706 and the pusher wire 702 during advancement of the pusher wire 702 through the sheath 706. It is contemplated that other orientation dependent features may be used on the sheath 706 and/or the locking element 708, as desired.

Figure 27:
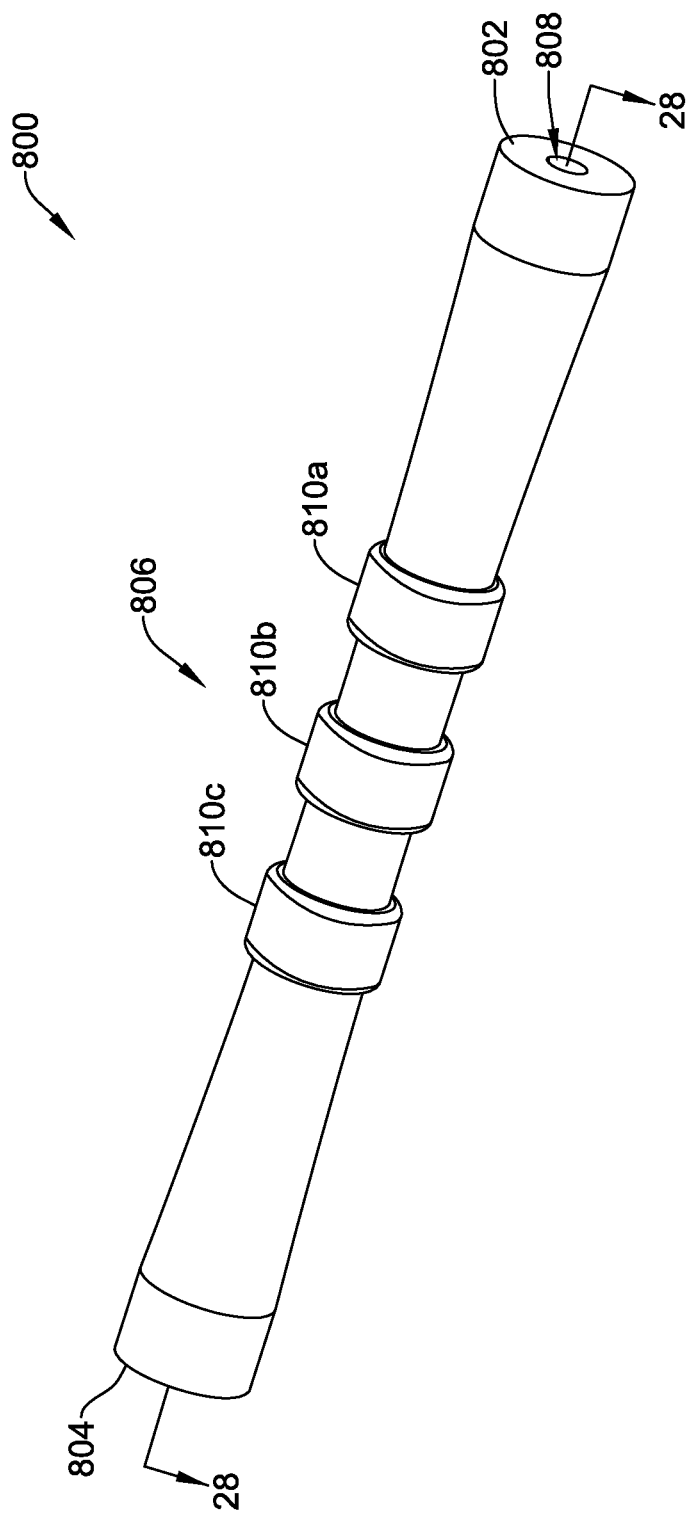
FIG. 27 is a perspective view of an illustrative locking mechanism.

FIG. 27 illustrates a perspective view of another illustrative locking element 800 which may include features configured to orientate the locking element 800 relative to a sheath, such as, but not limited to, the sheaths 106, 406, 506, 706, 706 described herein. The locking element 800 may be a tubular member having a proximal end 802, a distal end 804, and an intermediate region 806 positioned therebetween. The locking element 800 may have a generally hourglass shaped outer profile. For example, the outer diameter may generally decrease from the proximal end 802 towards the intermediate region 806 and increase from the intermediate region 806 to the distal end 804. However, this is not required. The outer profile of the locking element 800 may take any shape desired.

The locking element 800 may define a lumen 808 extending from the proximal end 802 to the distal end 804. A portion of the lumen 808 of the locking element 800 may be sized to slide freely over a sheath while another portion of the lumen 808 may be sized to exert a radially inward compressing force on the sheath. Thus, in some configurations, at least a portion of the sheath 706 may be radially inward of the locking element 800.

The intermediate region 806 may include plurality of raised regions or circumferential ribs 810a, 810b, 810c (collectively, 810). The circumferential ribs 810 may have an outer diameter 812 (see, for example, FIG. 28) that is greater than an outer diameter 814 (see, for example, FIG. 28) of the intermediate region 806 between the ribs 810. The circumferential ribs 810 may extend about an entire perimeter of the locking element 800 or less than an entire perimeter, as desired. It is contemplated that the circumferential ribs 810 may increase the tactility of the locking element 800 and/or make the locking element 800 easier to grip or handle. The number of circumferential ribs 810 (e.g., fewer than three or greater than three), the size of the circumferential ribs 810 (e.g., increasing or decreasing the diameter 812), the geometry of the circumferential ribs 810 (extending about less than an entire perimeter, having a different shape, etc.), and/or the spacing of the circumferential ribs 810 can be varied to enhance or diminish the tactility or gripability of the locking element 800, as desired.

The locking element 800 may be formed in a variety of different manners. For example, the locking element 800 may be injection molded, heat shrunk, 3-D printed, etc. The locking element 800 may be formed from a variety of different materials such as, but not limited to, hard or soft polymers, metals, composites, etc. It is further contemplated that that locking element 800 may be formed from a material that is more rigid than or stiffer than the outer sheath 706. For example, the material for the locking element 800 may be selected such that the locking element 800 does not deflect when the tapered portion of the lumen 808 of the locking element 800 is advanced over the sheath 706 but rather forces the sheath 706 to deflect inward. In some embodiments, the locking element 800 may be formed from a bright (or other) color easily noticeable by the user.

Figure 28:
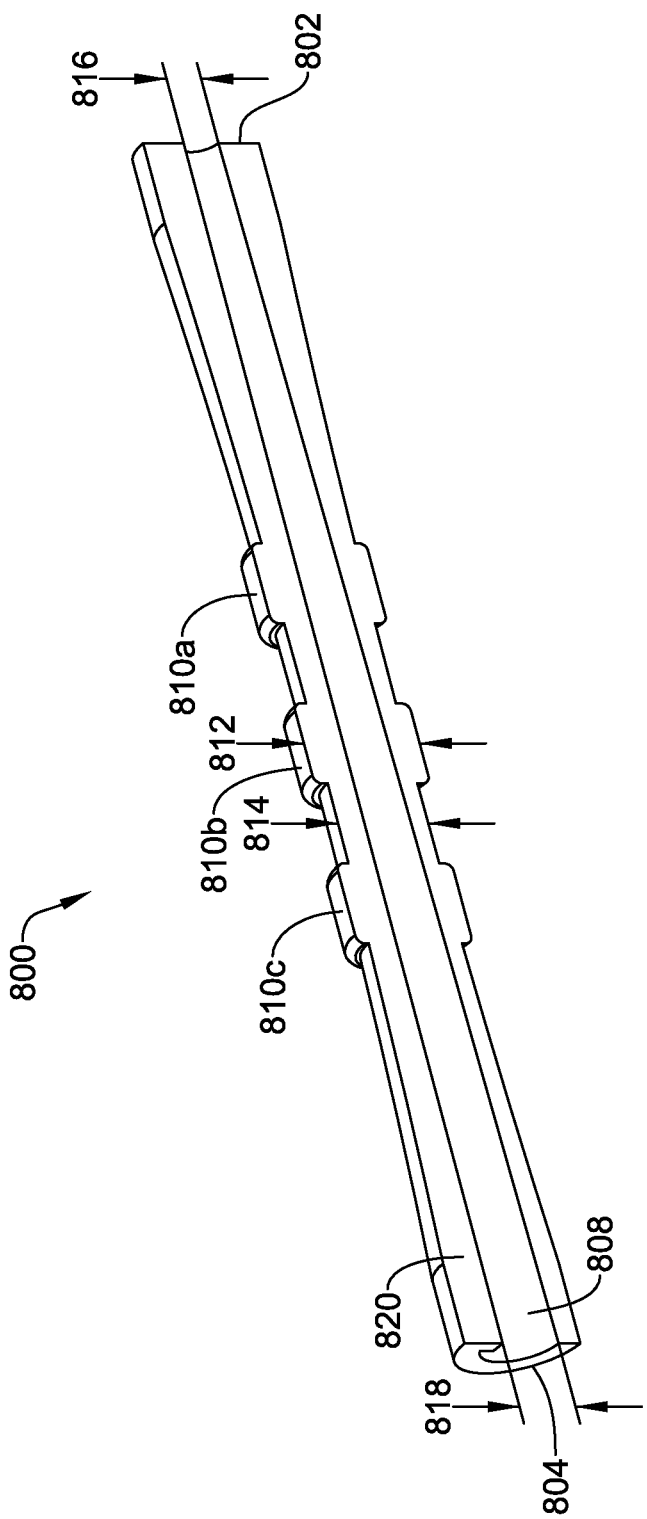
FIG. 28 is a perspective cross-sectional view of the illustrative locking mechanism of FIG. 27.
Figure 29:
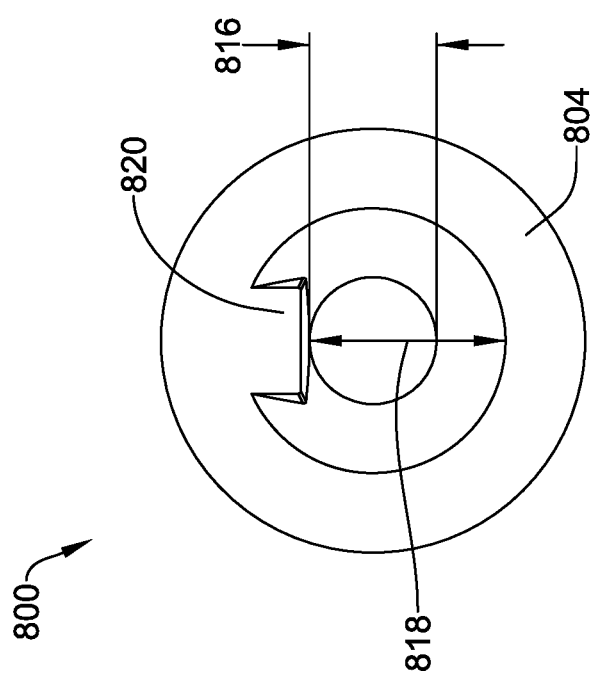
FIG. 29 is a distal end view of the illustrative locking mechanism of FIG. 27.

FIG. 28 is a distal end perspective cross-sectional view of the locking element 800 taken at line 28-28 of FIG. 27. FIG. 29 is a distal end view of the locking element 800. The locking element 800 may have a variable inner cross-sectional dimension. In some cases, the lumen 808 may have a generally tapered configuration. For example, in some embodiments, the lumen 808 of the locking element 800 may have a first cross-sectional dimension 816 adjacent to the proximal end 802 thereof which increases in the distal direction to a second cross-sectional dimension 818 adjacent to a distal end 804 thereof which is greater than the first cross-sectional dimension 816. The cross-sectional dimension may gradually transition in a tapered or sloped manner. In other embodiments, the cross-sectional dimension may vary in an abrupt or step-wise manner. These are just some examples. In some cases, a wall thickness of the locking element 800 may vary over at least a portion of the locking element. However, this is not required. The dimensions (e.g., inner diameter, outer diameter, length, slope, etc.) of the locking element 800 may be changed to create the desired locking effect (described in more detail herein). The distal inner cross-sectional dimension 818 may be sized such that the locking element 800 can slide freely over the sheath. The proximal, smaller inner cross-sectional dimension 816 may be sized to apply a compressive, or radially inward force on the outer surface of the sheath.

It is contemplated that the configuration of the locking element 800 may be adjusted to create the desired effect. For example, one or more of the inner cross-sectional dimensions 816, 818 may be made larger or smaller to accommodate different sizes of sheaths. In another example, the outer diameter of the locking element 800 may be increased or decreased to facilitate handling. It is further contemplated that the outer surface of the locking element 800 may include features to improve ergonomic handling, such as, but not limited to, bumps, waves, texturing, or indentations to improve gripability. In some cases, the sheath and/or the locking element 800 may include visual indicia to guide the user in manipulation of the locking element 800. In some cases, the overall length of the locking element 800 can be increased or decreased, as desired. It is further contemplated that the locking element 800 may be large enough to make it easy to handle but not so large as to be incompatible with other components, such as, but not limited to packaging.

The locking element 800 may further include an axially extending (e.g., parallel to a longitudinal axis of the locking element) protrusion 820 which extends radially inward from an inner surface of the locking element 80. The protrusion 820 may be a rectangular prism, such as, but not limited to a ridge or other three-dimensional structure configured to engage a mating groove, notch, or recess within the sheath. The protrusion 820 may be sized and shaped such that a distal portion of the locking element 800 can freely slide over the sheath when the protrusion 820 is aligned with a mating slot or recess of the sheath. As the locking element 800 is distally advanced, the lumen 808 narrows so as to exert a radially inward or compressive force on the sheath.

Together, the slot of the sheath and the protrusion 820 of the locking element 800 may create an orientation dependent assembly. For example, the locking element 800 is oriented such that the protrusion 820 is aligned with the slot of the sheath to allow the locking element 800 to distally advance over the sheath. Misalignment of the protrusion 820 and groove may lead to an interference between the locking element 800 and the sheath that would prevent passage of the sheath into the locking element 800 and subsequent locking of the pusher wire. This may prevent undesired re-engagement of the locking element 800 and sheath during use of the system in the event the locking element 800 is not fully removed from the pusher wire. In the absence of orientation dependent features, if the locking element 800 is left hanging on the pusher wire, it may unintendedly re-engage with the sheath and the pusher wire during advancement of the pusher wire through the sheath. It is contemplated that other orientation dependent features may be used on the sheath and/or the locking element 800, as desired.

While not explicitly shown, the locking element 800 may further include one or more features to provide a visual cue as to how the locking element 800 should be assembled with the sheath. For example, the features may include, but are not limited to, visual markings on an outer surface of the locking element 800 (e.g., arrows, words, etc.) or structural features, as desired.

In some embodiments, the medical device systems 100, 400, 500, 700 the pusher wire 102, 402, 502, 702, the implant 104, the sheath 106, 406, 506, 706, the locking element 108, 200, 300, 408, 508, 600, 708, 800, and/or components thereof, may be made from a metal, metal alloy, polymer (some examples of which are disclosed below), a metal-polymer composite, ceramics, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; platinum; palladium; gold; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. For example, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties. In at least some embodiments, portions or all of the medical device systems 100, 400, 500, 700, the pusher wire 102, 402, 502, 702, the implant 104, the sheath 106, 406, 506, 706, the locking element 108, 200, 300, 408, 508, 600, 708, 800, and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the medical device systems 100, 400, 500, 700, the pusher wire 102, 402, 502, 702, the implant 104, the sheath 106, 406, 506, 706, the locking element 108, 200, 300, 408, 508, 600, 708, 800, and/or components thereof, etc. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the medical device systems 100, 400, 500, 700, the pusher wire 102, 402, 502, 702, the implant 104, the sheath 106, 406, 506, 706, the locking element 108, 200, 300, 408, 508, 600, 708, 800, and/or components thereof, etc. to achieve the same result.

In some embodiments, a degree of Magnetic Resonance Imaging (MRI) compatibility is imparted into the medical device systems 100, 400, 500, 700, the pusher wire 102, 402, 502, 702, the implant 104, the sheath 106, 406, 506, 706, the locking element 108, 200, 300, 408, 508, 600, 708, 800, and/or components thereof, etc. For example, the medical device system 100, the pusher wire 102, the implant 104, the sheath 106, the locking element 108, 200, etc., and/or components or portions thereof, may be made of a material that does not substantially distort the image and create substantial artifacts (e.g., gaps in the image). Certain ferromagnetic materials, for example, may not be suitable because they may create artifacts in an MRI image. The medical device system 100, the pusher wire 102, the implant 104, the sheath 106, the locking element 108, 200, etc., or portions thereof, may also be made from a material that the MRI machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the medical device systems 100, 400, 500, 700, the pusher wire 102, 402, 502, 702, the implant 104, the sheath 106, 406, 506, 706, the locking element 108, 200, 300, 408, 508, 600, 708, 800, and/or components thereof, may be made from or include a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex® high-density polyethylene, Marlex® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some embodiments, the medical device systems 100, 400, 500, 700, the pusher wire 102, 402, 502, 702, the implant 104, the sheath 106, 406, 506, 706, the locking element 108, 200, 300, 408, 508, 600, 708, 800, and/or components thereof, etc. disclosed herein may include a fabric material disposed over or within the structure. The fabric material may be composed of a biocompatible material, such a polymeric material or biomaterial, adapted to promote tissue ingrowth. In some embodiments, the fabric material may include a bioabsorbable material. Some examples of suitable fabric materials include, but are not limited to, polyethylene glycol (PEG), nylon, polytetrafluoroethylene (PTFE, ePTFE), a polyolefinic material such as a polyethylene, a polypropylene, polyester, polyurethane, and/or or blends or combinations thereof.

In some embodiments, the medical device systems 100, 400, 500, 700, the pusher wire 102, 402, 502, 702, the implant 104, the sheath 106, 406, 506, 706, the locking element 108, 200, 300, 408, 508, 600, 708, 800, and/or components thereof, etc. may include and/or be formed from a textile material. Some examples of suitable textile materials may include synthetic yarns that may be flat, shaped, twisted, textured, pre-shrunk or un-shrunk. Synthetic biocompatible yarns suitable for use in the present invention include, but are not limited to, polyesters, including polyethylene terephthalate (PET) polyesters, polypropylenes, polyethylenes, polyurethanes, polyolefins, polyvinyl s, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun-types. The type and denier of the yarn chosen may be selected in a manner which forms a biocompatible and implantable prosthesis and, more particularly, a vascular structure having desirable properties.

In some embodiments, the medical device systems 100, 400, 500, 700, the pusher wire 102, 402, 502, 702, the implant 104, the sheath 106, 406, 506, 706, the locking element 108, 200, 300, 408, 508, 600, 708, 800, and/or components thereof, etc. may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl ketone, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A medical device system, comprising:
   a sheath having a proximal end, a distal end, an intermediate region disposed between the proximal end and the distal end, and a lumen extending from the proximal end to the distal end, the sheath further comprising a longitudinally extending slot extending distally from the proximal end of the sheath, the longitudinally extending slot terminating proximally of the intermediate region;
   a pusher wire slidably disposed within the lumen of the sheath, wherein a distal end of the pusher wire is configured to releasably engage an embolic coil positioned within the distal region of the lumen of the sheath; and
   a locking element configured to non-threadably engage the sheath, the locking element having a proximal end, a distal end, an intermediate region disposed between the proximal end and the distal end of the locking element, and a lumen extending from the proximal end to the distal end of the locking element, the lumen of the locking element having a generally hourglass shape;
   wherein a distal end region of the locking element is configured to freely slide over the proximal end of the sheath;
   wherein when the intermediate region of the locking element is disposed over the proximal end of the sheath, the locking element is configured to depress the sheath radially inwards onto a proximal end of the pusher wire.

2. The medical device system of claim 1, wherein the longitudinally extending slot of the sheath terminates at a circumferentially extending slit.

3. The medical device system of claim 1, wherein the sheath further comprises a first flap and a second flap adjacent the longitudinally extending slot.

4. The medical device system of claim 1, wherein the locking element has a first inner diameter adjacent the distal end of the locking element and a second inner diameter adjacent to the intermediate region of the locking element, the second inner diameter smaller than the first inner diameter.

5. The medical device system of claim 4, wherein the second inner diameter is generally constant and extends between a flared distal end region and a flared proximal end region.

6. The medical device system of claim 1, wherein the locking element is symmetrical about a plane oriented perpendicular to a central longitudinal axis of the locking element.

7. The medical device system of claim 1, wherein the locking element has a generally uniform wall thickness from the proximal end to the distal end of the locking element.

8. A medical device system, comprising:
   a sheath having a proximal end, a distal end, an intermediate region disposed between the proximal end and the distal end, and a lumen extending from the proximal end to the distal end, the sheath further comprising a pair of longitudinally extending slots each extending distally from the proximal end of the sheath and forming a pair of flexible arms therebetween;
   a pusher wire slidably disposed within the lumen of the sheath, wherein a distal end of the pusher wire is configured to releasably engage an implant positioned within the lumen of the sheath; and a locking element having a proximal end, a distal end, an intermediate region disposed between the proximal end and the distal end of the locking element, and a lumen extending from the proximal end to the distal end of the locking element, the lumen of the locking element having a generally hourglass shape;

wherein a distal end region of the locking element is configured to freely slide over the proximal end of the sheath;

wherein when the intermediate region of the locking element is disposed over the proximal end of the sheath, the locking element is configured to depress the pair of flexible arms radially inwards against a proximal end of the pusher wire;

wherein the locking element is symmetrical about a plane oriented perpendicular to a central longitudinal axis of the locking element.

9. The medical device system of claim 8, wherein the locking element has a first inner diameter adjacent the distal end of the locking element and a second inner diameter adjacent to the intermediate region of the locking element, the second inner diameter smaller than the first inner diameter.

10. The medical device system of claim 9, wherein the second inner diameter is generally constant and extends between a flared distal end region and a flared proximal end region.

11. The medical device system of claim 8, wherein the locking element has a generally uniform wall thickness from the proximal end to the distal end of the locking element.

12. A medical device system, comprising:

a sheath having a proximal end, a distal end, an intermediate region disposed between the proximal end and the distal end, and a lumen extending from the proximal end to the distal end, the sheath further comprising a longitudinally extending slot extending distally from the proximal end of the sheath;

a pusher wire slidably disposed within the lumen of the sheath, wherein a distal end of the pusher wire is configured to releasably engage an embolic coil positioned within the lumen of the sheath; and a locking element having a proximal end, a distal end, an intermediate region disposed between the proximal end and the distal end of the locking element, and a lumen extending from the proximal end to the distal end of the locking element, the lumen of the locking element having a generally hourglass shape;

wherein a distal end region of the locking element is configured to freely slide over the proximal end of the sheath; and wherein when the intermediate region of the locking element is disposed over the proximal end of the sheath, the locking element is configured to depress the sheath radially inwards against a proximal end of the pusher wire;

wherein the locking element has a generally uniform wall thickness from the proximal end to the distal end of the locking element.

13. The medical device system of claim 12, wherein the longitudinally extending slot of the sheath terminates at a circumferentially extending slit.

14. The medical device system of claim 12, wherein the sheath further comprises a first flap and a second flap adjacent the longitudinally extending slot.

15. The medical device system of claim 12, wherein the locking element has a first inner diameter adjacent the distal end of the locking element and a second inner diameter adjacent to the intermediate region of the locking element, the second inner diameter smaller than the first inner diameter.

16. The medical device system of claim 15, wherein the second inner diameter is generally constant and extends between a flared distal end region and a flared proximal end region.

17. The medical device system of claim 12, wherein the locking element is symmetrical about a plane oriented perpendicular to a central longitudinal axis of the locking element.

18. The medical device system of claim 12, wherein the locking element is configured to non-threadably engage the sheath.

* * * * *